(12) United States Patent
Andreas

(10) Patent No.: US 8,157,851 B2
(45) Date of Patent: *Apr. 17, 2012

(54) APPARATUS AND METHODS FOR DEPLOYMENT OF MULTIPLE CUSTOM-LENGTH PROSTHESES

(75) Inventor: Bernard H. Andreas, Redwood City, CA (US)

(73) Assignee: XTENT, Inc., Los Altos, CA (US)

( * ) Notice: Subject to any disclaimer, the term of this patent is extended or adjusted under 35 U.S.C. 154(b) by 308 days.

This patent is subject to a terminal disclaimer.

(21) Appl. No.: 11/148,545

(22) Filed: Jun. 8, 2005

(65) Prior Publication Data
US 2006/0282147 A1    Dec. 14, 2006

(51) Int. Cl.
*A61F 2/06* (2006.01)
(52) U.S. Cl. ..................................... 623/1.11
(58) Field of Classification Search .............. 623/1.11, 623/1.12; 606/108; 604/93.01, 250, 43
See application file for complete search history.

(56) References Cited

U.S. PATENT DOCUMENTS

| | | |
|---|---|---|
| 3,173,418 A | 3/1965 | Baran |
| 3,394,075 A | 7/1968 | Abramson |
| 3,938,502 A | 2/1976 | Bom |
| 4,292,974 A | 10/1981 | Fogarty et al. |
| 4,323,071 A | 4/1982 | Simpson et al. |
| 4,327,721 A | 5/1982 | Goldin et al. |
| 4,406,656 A | 9/1983 | Hattler et al. |
| 4,417,576 A | 11/1983 | Baran |
| 4,437,856 A | 3/1984 | Valli |
| 4,564,014 A | 1/1986 | Fogarty et al. |
| 4,576,177 A | 3/1986 | Webster, Jr. |
| 4,580,568 A | 4/1986 | Gianturci |
| 4,600,402 A * | 7/1986 | Rosenberg ............... 604/102.02 |
| 4,661,094 A | 4/1987 | Simpson |
| 4,665,918 A | 5/1987 | Garza et al. |
| 4,681,110 A | 7/1987 | Wiktor |
| 4,681,564 A | 7/1987 | Landreneau |
| 4,693,243 A | 9/1987 | Buras |
| 4,701,159 A * | 10/1987 | Brown et al. .................. 604/43 |
| 4,733,665 A | 3/1988 | Palmaz |
| 4,739,762 A | 4/1988 | Palmaz |
| 4,744,790 A | 5/1988 | Jankowski et al. |

(Continued)

FOREIGN PATENT DOCUMENTS

EP    274129 B1    7/1988

(Continued)

OTHER PUBLICATIONS

Born, N. et al."Early and recent intraluminal ultrasound devices," 1989, Internal Journal of Cardiac Imaging 4:79-88.

(Continued)

*Primary Examiner* — Tuan Nguyen
*Assistant Examiner* — Thomas McEvoy
(74) *Attorney, Agent, or Firm* — Levine Bagade Han LLP

(57) ABSTRACT

Apparatus for delivering stents to body lumens include one or more tubular prostheses carried at the distal end of a catheter shaft, a sheath slidably disposed over the prostheses, and a guidewire tube extending from within the sheath to the exterior of the sheath through an exit port in a sidewall thereof. A guidewire extends slidably through the guidewire tube. The sheath can be moved relative to the catheter shaft and the guidewire tube to expose the prostheses for deployment. Methods of delivering stents are also provided.

9 Claims, 20 Drawing Sheets

U.S. PATENT DOCUMENTS

| | | | |
|---|---|---|---|
| 4,762,129 A | 8/1988 | Bonzel | |
| 4,775,337 A | 10/1988 | Van Wagener et al. | |
| 4,775,371 A | 10/1988 | Mueller, Jr. | |
| 4,776,337 A | 10/1988 | Palmaz | |
| 4,790,315 A | 12/1988 | Mueller, Jr. et al. | |
| 4,839,623 A | 6/1989 | Schinstedt et al. | |
| 4,841,977 A | 6/1989 | Griffith et al. | |
| 4,850,358 A | 7/1989 | Millar | |
| 4,850,969 A | 7/1989 | Jackson | |
| 4,877,030 A | 10/1989 | Beck et al. | |
| 4,877,031 A | 10/1989 | Conway et al. | |
| 4,886,062 A | 12/1989 | Wiktor | |
| 4,892,519 A | 1/1990 | Songer et al. | |
| 4,911,163 A | 3/1990 | Fina | |
| 4,917,097 A | 4/1990 | Proudian et al. | |
| 4,950,227 A | 8/1990 | Savin et al. | |
| 4,950,232 A | 8/1990 | Ruzicka et al. | |
| 4,950,255 A * | 8/1990 | Brown et al. | 604/250 |
| 4,976,689 A | 12/1990 | Buchbinder et al. | |
| 4,988,356 A | 1/1991 | Crittenden et al. | |
| 4,994,033 A | 2/1991 | Shockey et al. | |
| 4,994,066 A | 2/1991 | Voss | |
| 4,994,069 A | 2/1991 | Ritchart et al. | |
| 5,000,734 A | 3/1991 | Boussignac et al. | |
| 5,007,897 A | 4/1991 | Kalb et al. | |
| 5,009,636 A | 4/1991 | Wortley et al. | |
| 5,014,089 A | 5/1991 | Sakashita et al. | |
| 5,015,232 A | 5/1991 | Maglinte | |
| 5,019,042 A | 5/1991 | Sahota | |
| 5,019,090 A | 5/1991 | Pinchuk | |
| 5,021,044 A | 6/1991 | Sharkawy | |
| 5,026,377 A | 6/1991 | Burton et al. | |
| 5,034,001 A | 7/1991 | Garrison et al. | |
| 5,041,089 A | 8/1991 | Mueller et al. | |
| 5,046,497 A | 9/1991 | Millar | |
| 5,049,132 A | 9/1991 | Shaffer et al. | |
| 5,087,244 A | 2/1992 | Wolinsky et al. | |
| 5,087,247 A | 2/1992 | Horn et al. | |
| 5,092,877 A | 3/1992 | Pinchuk | |
| 5,102,390 A | 4/1992 | Crittenden et al. | |
| 5,102,415 A | 4/1992 | Guenther et al. | |
| 5,102,417 A | 4/1992 | Palmaz | |
| 5,104,404 A | 4/1992 | Wolff | |
| 5,108,416 A | 4/1992 | Ryan et al. | |
| 5,112,303 A | 5/1992 | Pudenz et al. | |
| 5,112,305 A | 5/1992 | Barath et al. | |
| 5,123,917 A | 6/1992 | Lee | |
| 5,135,535 A | 8/1992 | Kramer | |
| 5,158,548 A | 10/1992 | Lau et al. | |
| 5,163,921 A | 11/1992 | Feiring | |
| 5,163,952 A | 11/1992 | Froix | |
| 5,180,364 A | 1/1993 | Ginsburg | |
| 5,180,366 A | 1/1993 | Woods | |
| 5,180,368 A | 1/1993 | Garrison | |
| 5,192,307 A | 3/1993 | Wall | |
| 5,195,984 A | 3/1993 | Schatz | |
| 5,203,338 A | 4/1993 | Jang | |
| 5,213,576 A | 5/1993 | Abiuso et al. | |
| 5,217,495 A | 6/1993 | Kaplan et al. | |
| 5,219,326 A | 6/1993 | Hattler | |
| 5,219,335 A | 6/1993 | Willard et al. | |
| 5,219,355 A | 6/1993 | Parodi et al. | |
| 5,226,888 A | 7/1993 | Arney | |
| 5,226,913 A | 7/1993 | Pinchuk | |
| 5,242,396 A | 9/1993 | Evard | |
| 5,242,399 A | 9/1993 | Lau et al. | |
| 5,242,451 A | 9/1993 | Harada et al. | |
| 5,246,421 A | 9/1993 | Saab | |
| 5,254,089 A | 10/1993 | Wang | |
| 5,257,974 A | 11/1993 | Cox | |
| 5,266,073 A | 11/1993 | Wall | |
| 5,273,536 A | 12/1993 | Savas | |
| 5,281,200 A | 1/1994 | Corso, Jr. et al. | |
| 5,282,785 A | 2/1994 | Shapland et al. | |
| 5,284,473 A | 2/1994 | Calabria | |
| 5,295,962 A | 3/1994 | Crocker et al. | |
| 5,300,085 A | 4/1994 | Yock | |
| 5,306,250 A | 4/1994 | March et al. | |
| 5,308,356 A | 5/1994 | Blackshear, Jr. et al. | |
| 5,318,535 A | 6/1994 | Miraki | |
| 5,344,187 A | 9/1994 | Kreis et al. | |
| 5,344,401 A | 9/1994 | Radisch et al. | |
| 5,344,426 A | 9/1994 | Lau et al. | |
| 5,358,487 A | 10/1994 | Miller | |
| 5,360,401 A | 11/1994 | Turnland et al. | |
| 5,360,443 A | 11/1994 | Barone et al. | |
| 5,364,356 A | 11/1994 | Hafling | |
| 5,370,617 A | 12/1994 | Sahota | |
| 5,378,237 A | 1/1995 | Boussignac et al. | |
| 5,382,261 A | 1/1995 | Palmaz | |
| 5,395,333 A | 3/1995 | Brill | |
| 5,409,495 A | 4/1995 | Osborn | |
| 5,411,507 A | 5/1995 | Heckele | |
| 5,415,637 A | 5/1995 | Khosravi | |
| 5,421,955 A | 6/1995 | Lau et al. | |
| 5,425,709 A | 6/1995 | Gambale | |
| 5,433,706 A | 7/1995 | Abiuso | |
| 5,439,445 A | 8/1995 | Kontos | |
| 5,443,500 A | 8/1995 | Sigwart | |
| 5,445,646 A | 8/1995 | Euteneuer et al. | |
| 5,478,119 A * | 12/1995 | Dye | 285/26 |
| 5,478,349 A | 12/1995 | Nicholas | |
| 5,501,227 A | 3/1996 | Yock | |
| 5,507,768 A | 4/1996 | Lau et al. | |
| 5,507,771 A | 4/1996 | Gianturco | |
| 5,514,093 A | 5/1996 | Ellis et al. | |
| 5,514,154 A | 5/1996 | Lau et al. | |
| 5,527,354 A | 6/1996 | Fontaine et al. | |
| 5,534,007 A | 7/1996 | St. Germain et al. | |
| 5,545,209 A | 8/1996 | Roberts et al. | |
| 5,549,551 A | 8/1996 | Peacock et al. | |
| 5,549,563 A | 8/1996 | Kronner | |
| 5,549,635 A | 8/1996 | Solar | |
| 5,554,181 A | 9/1996 | Das | |
| 5,562,725 A | 10/1996 | Schmitt et al. | |
| 5,569,205 A * | 10/1996 | Hart et al. | 604/167.03 |
| 5,571,086 A | 11/1996 | Kaplan et al. | |
| 5,591,222 A | 1/1997 | Susawa et al. | |
| 5,607,463 A | 3/1997 | Schwartz et al. | |
| 5,620,457 A | 4/1997 | Pinchasik et al. | |
| 5,628,775 A | 5/1997 | Jackson et al. | |
| 5,634,928 A | 6/1997 | Fischell et al. | |
| 5,676,654 A | 10/1997 | Ellis et al. | |
| 5,683,451 A | 11/1997 | Lenker et al. | |
| 5,697,948 A | 12/1997 | Marin et al. | |
| 5,722,669 A | 3/1998 | Shimizu et al. | |
| 5,735,869 A | 4/1998 | Fernandez-Aceytuno | |
| 5,749,848 A | 5/1998 | Jang et al. | |
| 5,755,772 A | 5/1998 | Evans et al. | |
| 5,755,776 A | 5/1998 | Al-Saadon | |
| 5,755,781 A | 5/1998 | Jayaraman | |
| 5,769,882 A | 6/1998 | Fogarty et al. | |
| 5,772,669 A | 6/1998 | Vrba | |
| 5,776,141 A | 7/1998 | Klein et al. | |
| 5,807,398 A | 9/1998 | Shaknovich | |
| 5,824,040 A | 10/1998 | Cox et al. | |
| 5,824,041 A | 10/1998 | Lenker et al. | |
| 5,833,694 A | 11/1998 | Poncet | |
| 5,836,964 A | 11/1998 | Richter et al. | |
| 5,843,092 A | 12/1998 | Heller et al. | |
| 5,857,999 A * | 1/1999 | Quick et al. | 604/107 |
| 5,858,556 A | 1/1999 | Eckert et al. | |
| 5,870,381 A | 2/1999 | Kawasaki et al. | |
| 5,879,370 A | 3/1999 | Fischell et al. | |
| 5,891,190 A | 4/1999 | Boneau | |
| 5,895,398 A | 4/1999 | Wensel et al. | |
| 5,902,332 A | 5/1999 | Schatz | |
| 5,961,536 A | 10/1999 | Mickley et al. | |
| 5,976,155 A | 11/1999 | Foreman et al. | |
| 5,980,484 A | 11/1999 | Ressemann et al. | |
| 5,980,486 A | 11/1999 | Enger | |
| 5,980,552 A | 11/1999 | Pinchasik et al. | |
| 5,984,957 A | 11/1999 | Laptewicz, Jr. et al. | |
| 6,007,517 A | 12/1999 | Anderson | |
| 6,022,359 A | 2/2000 | Frantzen | |
| 6,033,434 A | 3/2000 | Borghi | |
| 6,056,722 A | 5/2000 | Jayaraman | |

| | | |
|---|---|---|
| 6,066,155 A | 5/2000 | Amann et al. |
| 6,068,655 A | 5/2000 | Seguin et al. |
| 6,090,063 A | 7/2000 | Makower et al. |
| 6,090,136 A | 7/2000 | McDonald et al. |
| 6,106,530 A | 8/2000 | Harada |
| RE36,857 E | 9/2000 | Euteneuer et al. |
| D431,651 S * | 10/2000 | Molina .................. D24/129 |
| 6,126,685 A | 10/2000 | Lenker et al. |
| 6,143,016 A | 11/2000 | Bleam et al. |
| 6,165,167 A | 12/2000 | Delaloye |
| 6,179,878 B1 | 1/2001 | Duerig et al. |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,241,691 B1 | 6/2001 | Ferrera et al. |
| 6,248,092 B1 * | 6/2001 | Miraki et al. ............ 604/96.01 |
| 6,251,132 B1 | 6/2001 | Ravenscroft et al. |
| 6,251,134 B1 | 6/2001 | Alt et al. |
| 6,254,628 B1 | 7/2001 | Wallace et al. |
| 6,258,117 B1 | 7/2001 | Camrud et al. |
| 6,273,913 B1 | 8/2001 | Wright et al. |
| 6,312,458 B1 | 11/2001 | Golds |
| 6,315,794 B1 | 11/2001 | Richter |
| 6,319,277 B1 | 11/2001 | Rudnick et al. |
| 6,357,104 B1 | 3/2002 | Myers |
| 6,375,676 B1 | 4/2002 | Cox |
| 6,383,171 B1 | 5/2002 | Gifford et al. |
| 6,419,693 B1 | 7/2002 | Fariabi |
| 6,451,025 B1 | 9/2002 | Jervis |
| 6,451,050 B1 | 9/2002 | Rudakov et al. |
| 6,468,298 B1 | 10/2002 | Pelton |
| 6,468,299 B2 | 10/2002 | Stack et al. |
| 6,482,179 B1 * | 11/2002 | Chu et al. ................ 604/164.09 |
| 6,485,510 B1 | 11/2002 | Camrud et al. |
| 6,488,694 B1 | 12/2002 | Lau et al. |
| 6,511,468 B1 | 1/2003 | Cragg et al. |
| 6,520,987 B1 | 2/2003 | Plante |
| 6,527,789 B1 | 3/2003 | Lau et al. |
| 6,527,799 B2 | 3/2003 | Shanley |
| 6,551,270 B1 * | 4/2003 | Bimbo et al. ............ 604/93.01 |
| 6,555,157 B1 | 4/2003 | Hossainy |
| 6,575,993 B1 | 6/2003 | Yock |
| 6,582,394 B1 | 6/2003 | Reiss et al. |
| 6,592,549 B2 | 7/2003 | Gerdts et al. |
| 6,605,062 B1 | 8/2003 | Hurley et al. |
| 6,645,547 B1 | 11/2003 | Shekalim et al. |
| 6,656,212 B2 | 12/2003 | Ravenscroft et al. |
| 6,666,883 B1 | 12/2003 | Seguin et al. |
| 6,679,909 B2 | 1/2004 | McIntosh et al. |
| 6,692,465 B2 | 2/2004 | Kramer |
| 6,702,843 B1 | 3/2004 | Brown |
| 6,712,827 B2 | 3/2004 | Ellis et al. |
| 6,712,845 B2 | 3/2004 | Hossainy |
| 6,723,071 B2 | 4/2004 | Gerdts et al. |
| 6,743,251 B1 | 6/2004 | Eder |
| 6,827,710 B1 * | 12/2004 | Mooney et al. .............. 604/500 |
| 7,323,006 B2 * | 1/2008 | Andreas et al. ............ 623/1.11 |
| 7,594,911 B2 * | 9/2009 | Powers et al. .............. 604/533 |
| 2001/0020181 A1 | 9/2001 | Layne |
| 2001/0044595 A1 | 11/2001 | Reydel et al. |
| 2002/0138132 A1 | 9/2002 | Brown |
| 2002/0151955 A1 | 10/2002 | Tran et al. |
| 2002/0156496 A1 | 10/2002 | Chermoni |
| 2002/0188343 A1 | 12/2002 | Mathis |
| 2002/0188347 A1 | 12/2002 | Mathis |
| 2003/0032941 A1 * | 2/2003 | Boyle et al. .................. 604/533 |
| 2003/0045923 A1 | 3/2003 | Bashiri et al. |
| 2003/0114919 A1 | 6/2003 | McQuiston et al. |
| 2003/0114922 A1 | 6/2003 | Iwasaka et al. |
| 2003/0139796 A1 | 7/2003 | Sequin et al. |
| 2003/0139797 A1 | 7/2003 | Johnson et al. |
| 2003/0176909 A1 | 9/2003 | Kusleika |
| 2003/0199821 A1 | 10/2003 | Gerdts et al. |
| 2004/0087965 A1 | 5/2004 | Levine et al. |
| 2004/0098081 A1 * | 5/2004 | Landreville et al. ......... 623/1.11 |
| 2006/0095005 A1 * | 5/2006 | Quinn et al. ............. 604/103.04 |

FOREIGN PATENT DOCUMENTS

| | | |
|---|---|---|
| EP | 282143 | 9/1988 |
| EP | 533960 | 3/1993 |
| EP | 203945 B2 | 12/1996 |
| WO | WO 87/07510 | 12/1987 |
| WO | WO 88/09682 | 12/1988 |
| WO | WO 92/11890 | 7/1992 |
| WO | WO 92/11895 | 7/1992 |
| WO | WO 93/21985 | 11/1993 |
| WO | WO 94/11048 | 5/1994 |
| WO | WO 94/11053 | 5/1994 |
| WO | WO 95/03081 | 2/1995 |
| WO | WO 95/03082 | 2/1995 |
| WO | WO 95/11055 | 4/1995 |
| WO | WO 96/33677 | 10/1996 |
| WO | WO 97/46174 | 12/1997 |
| WO | WO 99/01087 A1 | 1/1999 |
| WO | WO 00/15151 A1 | 3/2000 |
| WO | WO 00/32136 A1 | 6/2000 |
| WO | WO 00/41649 A1 | 7/2000 |
| WO | WO 01/91918 | 12/2001 |
| WO | WO 03/022178 A1 | 3/2003 |
| WO | WO 03/051425 | 6/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 | 6/2004 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

Hong, M. K. et al. "A New PTCA Balloon Catheter With Intramural Channels For Local Delivery of Drugs at Low Pressure," 1992, Supplement to Circulation, Abstracts From the 65th Scientific Sessions, vol. 86, No. 4, #1514.

Stimpson et al, Parallel Production of Oligonucleotide Arrays Using Membranes and Reagent Jet Printing, BioTechniques 25:886-890 (Nov. 1998).

* cited by examiner

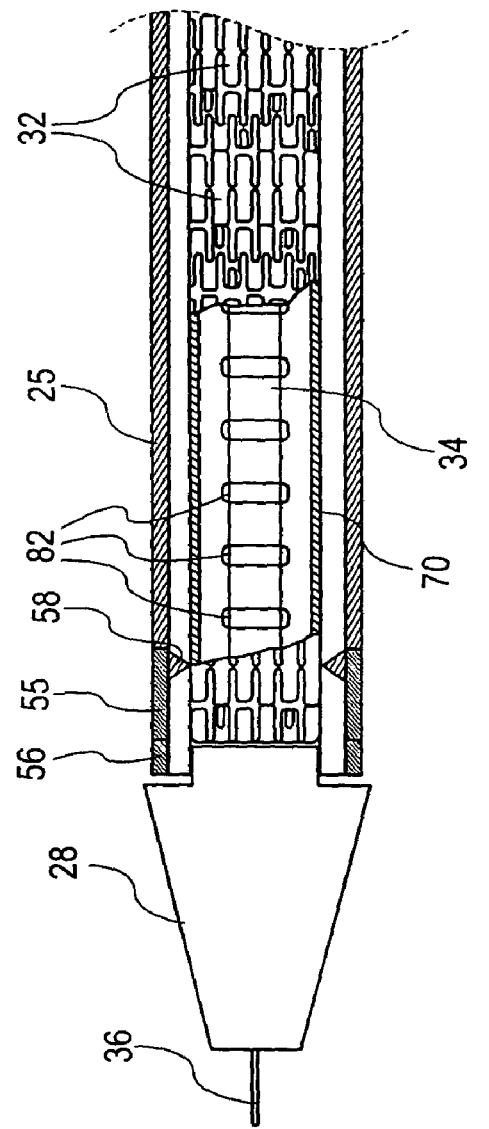

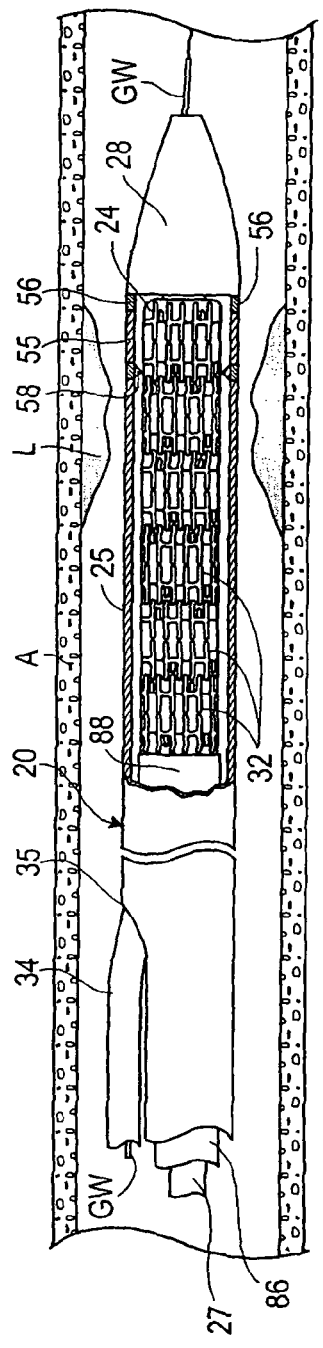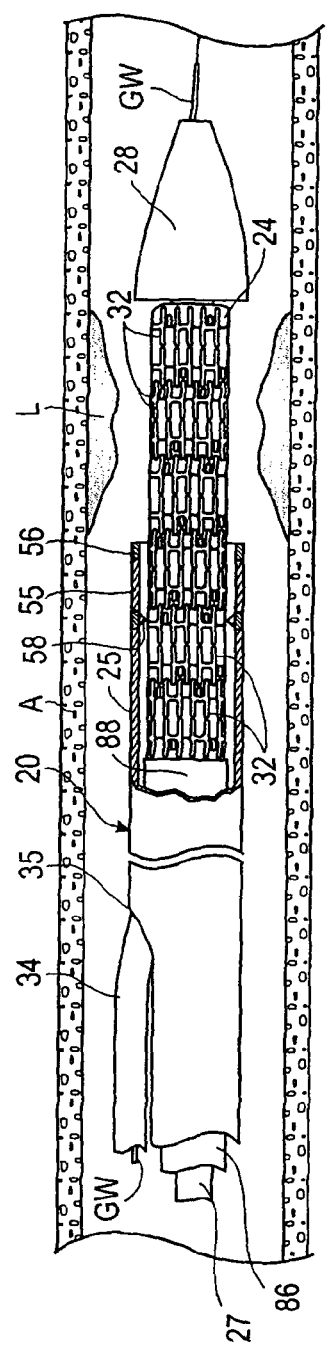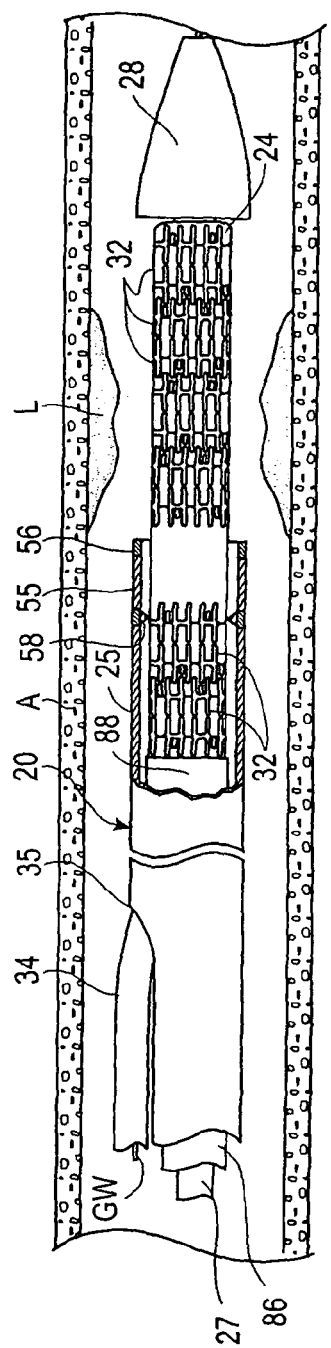

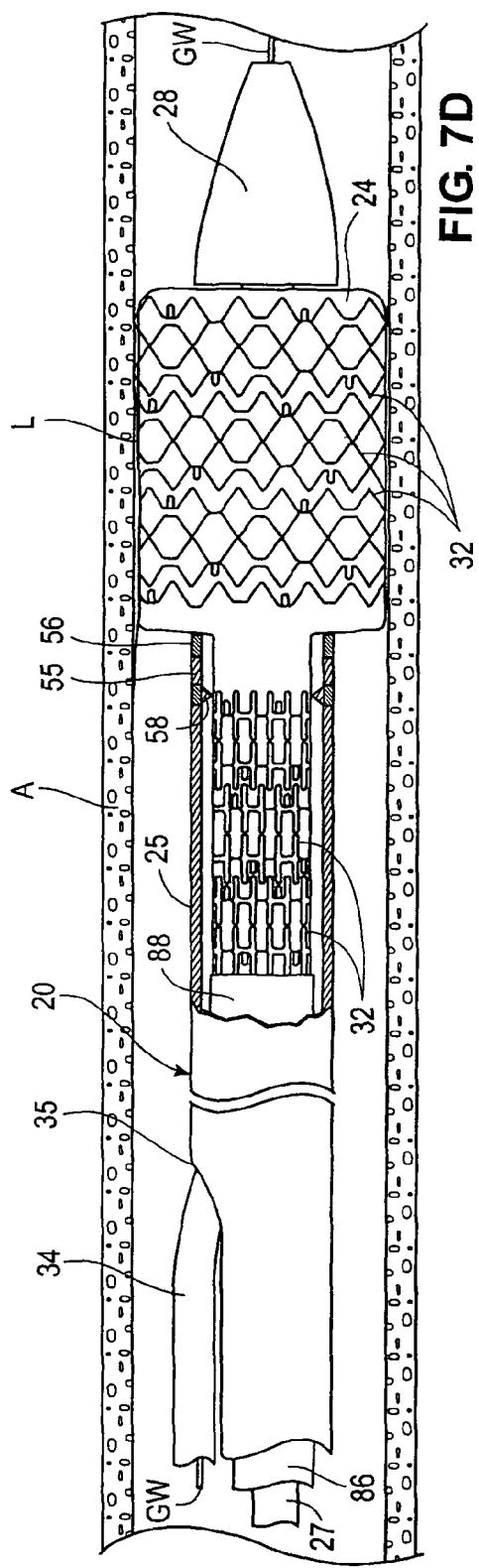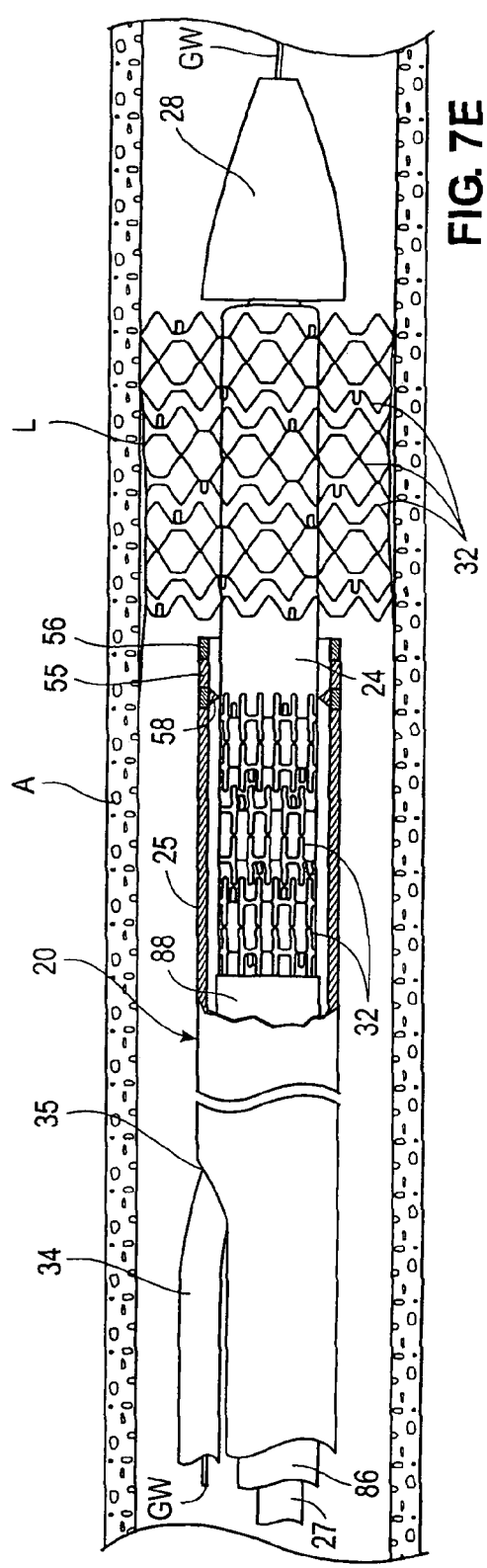

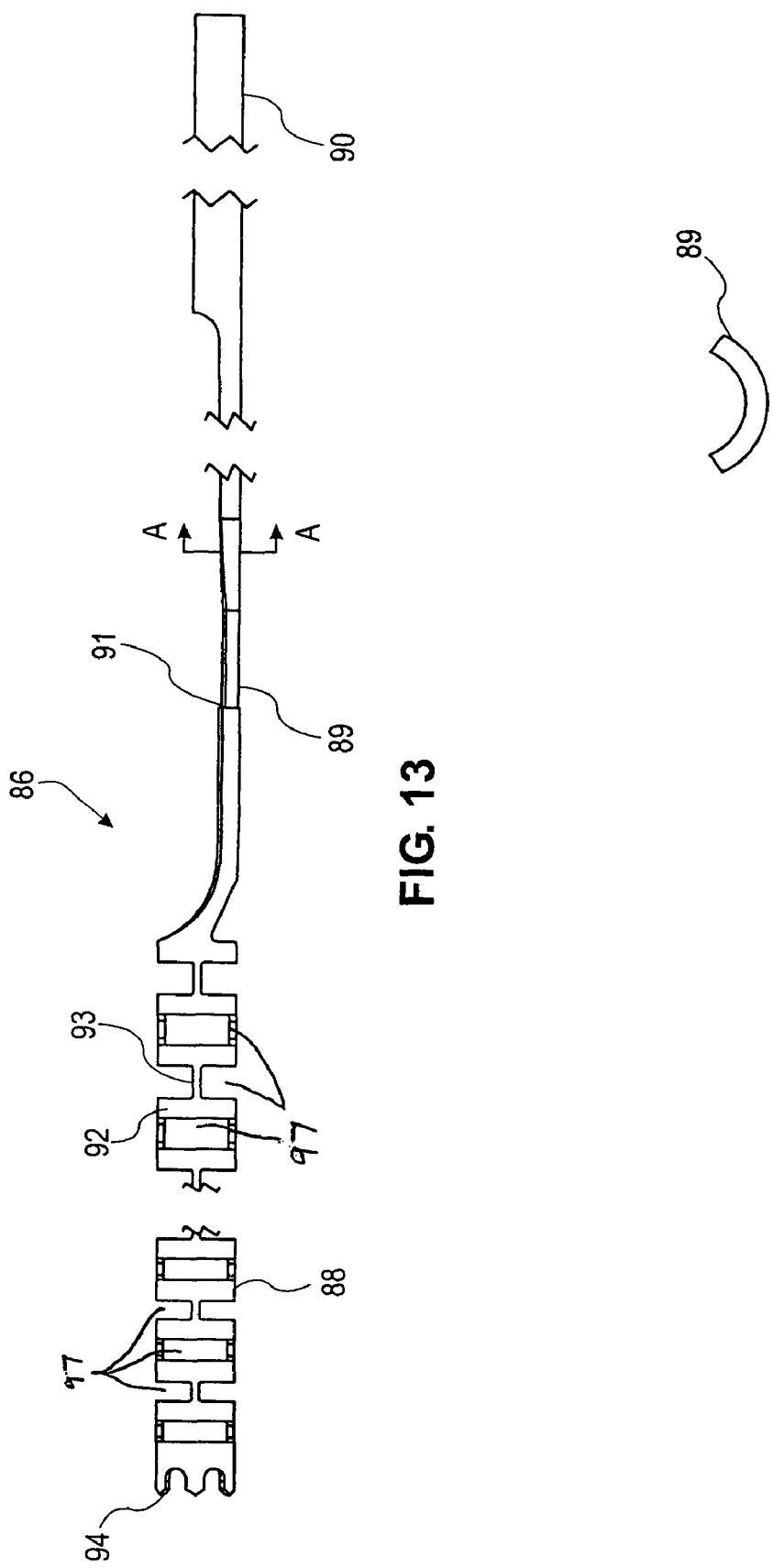

APPARATUS AND METHODS FOR DEPLOYMENT OF MULTIPLE CUSTOM-LENGTH PROSTHESES

FIELD OF THE INVENTION

This invention relates generally to vascular catheters, and more specifically to stents and stent delivery catheters for deployment in the coronary arteries and other vessels.

BACKGROUND OF THE INVENTION

Stenting has become an increasingly important treatment option for patients with coronary artery disease. Stenting involves the placement of a tubular prosthesis within a diseased coronary artery to expand the arterial lumen and maintain the patency of the artery. Early stent technology suffered from problems with restenosis, the tendency of the coronary artery to become re-occluded following stent placement. However, in recent years, restenosis rates have decreased dramatically. As a result, the number of stenting procedures being performed in the United States, Europe, and elsewhere has soared.

Stents are delivered to the coronary arteries using long, flexible vascular catheters typically inserted through a femoral artery. For self-expanding stents, the stent is simply released from the delivery catheter and it resiliently expands into engagement with the vessel wall. For balloon expandable stents, a balloon on the delivery catheter is expanded which expands and deforms the stent to the desired diameter, whereupon the balloon is deflated and removed.

Current stent delivery technology, however, suffers from a number of drawbacks. For example, current stent delivery catheters are not capable of customizing the length of the stent in situ to match the size of the lesion to be treated. While lesion size may be measured prior to stenting using angiography or fluoroscopy, such measurements may be inexact. If a stent is introduced that is found to be of inappropriate size, the delivery catheter and stent must be removed from the patient and replaced with a different device of correct size.

Moreover, current stent delivery devices cannot treat multiple lesions with a single catheter. Current devices are capable of delivering only a single stent with a single catheter, and if multiple lesions are to be treated, a new catheter and stent must be introduced for each lesion to be treated.

Further, current stent delivery devices are not well-adapted for treating vascular lesions that are very long and/or in curved regions of a vessel. Current stents have a discrete length that is relatively short due to their stiffness. If current stents were made longer so as to treat longer lesions, they would not conform well to the curvature of vessels or to the movement of vessels on the surface of the beating heart. On the other hand, any attempt to place multiple stents end-to-end in longer lesions is hampered by the inability to maintain appropriate inter-stent spacing and to prevent overlap of adjacent stents.

Additionally, some stent delivery catheters and angioplasty balloon catheters, particularly those having movable external sheaths to enclose the stent or balloon, suffer from poor tracking and cumbersome interaction with guidewires. Some such catheters utilize an "over-the-wire" design in which the guidewire extends through an inner lumen of the catheter from its proximal end to its distal end, a design that makes catheter exchanges cumbersome and time-consuming. Rapid exchange designs have also been proposed for such catheters wherein the guidewire extends through the distal end of the catheter and out through a port in a sidewall of the sheath. However, in these designs the guidewire inhibits smooth retraction of the sheath and, if the sheath is retracted a substantial distance, the port can become so displaced from the distal end of the catheter that the guidewire does not slide smoothly as the catheter is moved.

Finally, many stent delivery catheters suffer from inflexibility and high cross-sectional profile, which hamper endovascular positioning.

For these and other reasons, stents and stent delivery catheters are needed which enable the customization of stent length in situ, and the treatment of multiple lesions of various sizes, without requiring removal of the delivery catheter from the patient. Such stents and stent delivery catheters should be capable of treating lesions of particularly long length and lesions in curved regions of a vessel, and should be highly flexible to conform to vessel shape and movement. Such stent delivery catheters should further be of minimal cross-sectional profile and should be highly flexible for endovascular positioning through tortuous vascular pathways.

BRIEF SUMMARY OF THE INVENTION

The invention provides apparatus and methods for delivering prostheses or stents into body lumens. In one aspect of the invention, an apparatus for delivering a prosthesis into a target vessel comprises a flexible catheter shaft having proximal and distal ends and a first lumen therein. A tubular prosthesis is releasably carried near the distal end of the catheter shaft and is expandable to a shape suitable for engaging the target vessel. A sheath is disposed over the catheter shaft and the tubular prosthesis and is axially movable relative thereto. The sheath has proximal and distal ends, a sidewall, and an exit port in the sidewall between the proximal and distal ends. A guidewire tube extends through the exit port and has a distal extremity disposed within the tubular prosthesis and a proximal extremity disposed outside of the sheath, the guidewire tube being adapted for slidably receiving a guidewire therethrough.

Preferably, the guidewire tube is slidable through the exit port so that the sheath slides relative to the guidewire tube as it is retracted to expose the prosthesis for deployment. Usually the guidewire tube is fixed relative to the catheter shaft, and may be attached thereto. If an expandable member is mounted to the catheter shaft for prosthesis expansion, the guidewire tube may extend through and attach to the expandable member.

Because the guidewire tube exits the sheath in a distal extremity thereof the sheath has a low profile portion proximal to the exit port that has a smaller diameter than the portion distal to the exit port. Not only does this reduce the cross-sectional profile, but increases the flexibility of the device.

The exit port may be cut into the sidewall of the sheath to face laterally, or alternatively oriented so as to face generally in a proximal direction. The exit port is usually positioned so as to be closer to the distal end of the sheath than to the proximal end thereof, and is preferably a distance of about 20-35 cm from the distal end of the sheath. With the sheath advanced fully distally over the catheter shaft, the proximal extremity of the guidewire tube exposed outside the sheath is preferably about 3-15 cm in length, although various lengths are possible, even as long or longer than the catheter shaft itself. The proximal end of the guidewire tube is preferably disposed a distance of less than about one-half the length of the catheter shaft from the distal end thereof, but in some embodiments may extend further proximally, even as far as the proximal end of the catheter shaft.

The apparatus of the invention may be configured to deliver tubular prostheses that are either self-expanding or expandable by a balloon or other expandable member. When self-expanding prostheses are used, the sheath is adapted to constrain the prosthesis in a collapsed configuration. Upon retraction of the sheath, the prosthesis is released and self-expands to engage the vessel.

For balloon-expandable prostheses, an expandable member is mounted to the catheter shaft near the distal end thereof. The tubular prosthesis is positionable over the expandable member for expansion therewith. Usually the expandable member will comprise a balloon in communication with an inflation lumen in the catheter shaft for delivery of inflation fluid to the balloon. The sheath is axially positionable relative to the expandable member and configured to restrain expansion of a selected portion of the expandable member. Preferably the sheath is reinforced to prevent expansion thereof by the expandable member.

In a preferred aspect of the invention, the tubular prosthesis comprises a plurality of prosthesis segments. The sheath is axially movable relative to the prosthesis segments and configured to restrain expansion of a selectable number of prosthesis segments. In this way, lesions of various lengths may be treated by adjusting the length of the prosthesis in situ, without removal of the device from the body. In these embodiments, a pusher may be slidably disposed within the sheath proximal to the tubular prosthesis. The pusher has a distal end in engagement with the tubular prosthesis for moving the tubular prosthesis relative to the catheter shaft.

In a further aspect of the invention, a method of delivering a prosthesis in a target vessel of a patient comprises inserting a guidewire through the patient's vasculature to the target vessel; slidably coupling a delivery catheter to the guidewire, the delivery catheter having a sheath and a guidewire tube, a proximal extremity of the guidewire tube being outside the sheath and a distal extremity of the guidewire tube being inside the sheath, the guidewire being slidably positioned through the guidewire tube; advancing the delivery catheter over the guidewire to the target vessel; retracting the sheath relative to the guidewire tube to expose a tubular prosthesis carried by the delivery catheter; and expanding the tubular prosthesis into engagement with the target vessel.

Usually, the guidewire tube will extend through an exit port in the sheath, and the guidewire tube will slide through the exit port as the sheath is retracted. The method may include sealing the exit port around the guidewire tube to restrict fluid flow therethrough, but preferably the exit port allows some fluid flow to provide flushing of the distal portion of the catheter.

In a preferred embodiment, an expandable member is fixed to a distal portion of the guidewire tube and the tubular prosthesis is positionable over the expandable member. The sheath is slidably disposed over the prosthesis and the expandable member and may be retracted a selectable distance to expose a desired length of the prosthesis and expandable member. The tubular prosthesis will then be expanded by expanding the expandable member. The sheath may be used to cover a proximal portion of the expandable member to constrain the proximal portion from expansion while a distal portion of the expandable member expands. Usually, the expandable member is inflatable and will be inflated by delivering inflation fluid to the expandable member through an inflation lumen in the catheter shaft. The guidewire tube preferably extends through the interior of the expandable member, which may be attached to the guidewire tube.

In a preferred aspect of the invention, the tubular prosthesis comprises a plurality of prosthesis segments, and the method includes positioning a first selected number of the prosthesis segments on the expandable member for expansion therewith. The method may further include positioning the sheath over a second selected number of the prosthesis segments to constrain expansion thereof. The first selected number of prosthesis segments may be positioned on the expandable member by pushing the first selected number with a pusher that is axially slidable relative to the expandable member.

In alternative embodiments, the tubular prosthesis self-expands when the sheath is retracted. In embodiments in which the prosthesis comprises multiple prosthesis segments, the sheath may be retracted relative to a selected number of such segments to allow the segments to self-expand into contact with the vessel.

In another aspect, the invention provides a balloon catheter for treating a target vessel that includes a flexible catheter shaft having proximal and distal ends and a first lumen therein. An expandable member is connected to the catheter shaft, and a sheath is disposed over the catheter shaft and the expandable member and is axially movable relative thereto. The sheath has an exit port in a sidewall thereof between its proximal and distal ends. A guidewire tube extends through the exit port and has a proximal extremity disposed outside of the sheath and a distal extremity disposed within the sheath that is coupled to the catheter shaft or the expandable member or both. The guidewire tube is adapted for slidably receiving a guidewire therethrough. The expandable member preferably comprises a balloon in fluid communication with the first lumen to receive inflation fluid therefrom. The sheath may be positionable to constrain a first selected portion of the expandable member from expansion while a second selected portion of the expandable member expands.

In a preferred embodiment of the balloon catheter of the invention, a tubular prosthesis is disposed on the expandable member and is expandable therewith. The tubular prosthesis will preferably comprise a plurality of unconnected stent segments that are slidable relative to the expandable member. The sheath is positionable to expose a first selected portion of the stent segments while covering a second selected portion of the stent segments.

In yet another aspect of the invention, an apparatus for delivering a prosthesis into a target vessel comprises a flexible catheter shaft having proximal and distal ends and a tubular prosthesis slidably coupled to the catheter shaft, the tubular prosthesis being expandable to a shape suitable for engaging the target vessel. A pusher is provided for moving the tubular prosthesis from a pre-deployment position to a deployment position near the distal end of the catheter shaft. The apparatus further includes a stop on the catheter shaft configured to engage the tubular prosthesis when the tubular prosthesis is in the deployment position.

In one embodiment, an expandable member is coupled to the catheter shaft and the tubular prosthesis is adapted for expansion by the expandable member. The expandable member, e.g. balloon, has an interior, and the stop is preferably disposed within the interior of the expandable member. The stop may also be disposed outside of or on the exterior surface of the expandable member. Alternatively, the tubular prosthesis is self-expanding and expands upon being released from the catheter shaft.

In a preferred aspect, a plurality of tubular prostheses are slidably coupled to the catheter shaft and are movable by the pusher to the deployment position. In addition, a sheath may be movably coupled to the catheter shaft and positionable over the tubular prosthesis or prostheses.

In a further method of deploying a tubular prosthesis in a target vessel according to the invention a catheter shaft is positioned in a target vessel and the tubular prosthesis is moved distally relative to the catheter shaft while the catheter shaft remains in the target vessel until the prosthesis engages a stop near the distal end of the catheter shaft. The tubular prosthesis is then expanded to engage a wall of the target vessel.

After expanding the tubular prosthesis, a second prosthesis (or any number of additional prostheses) may be moved distally relative to the catheter shaft until the second prosthesis engages the stop, and the second prosthesis then expanded to engage a wall of the target vessel. Alternatively, a second prosthesis may be moved distally relative to the catheter shaft simultaneously with moving the tubular prosthesis, and both the second prosthesis and the tubular prosthesis are expanded together to engage the wall of the target vessel. Usually, the tubular prosthesis and any additional prostheses are moved by a pusher movably coupled to the catheter shaft.

The tubular prosthesis is preferably expanded by inflating a balloon coupled to the catheter shaft. Alternatively, the tubular prosthesis may be self-expandable.

Further, the method may include retaining a second prosthesis in an unexpanded configuration on the catheter shaft while the tubular prosthesis is expanded. In one embodiment, the second prosthesis is retained within a sheath movably coupled to the catheter shaft.

Further aspects of the nature and advantages of the invention will become apparent from the detailed description below taken in conjunction with the drawings.

BRIEF DESCRIPTION OF THE DRAWINGS

FIG. 2C is a side cross-section of a distal portion of a stent delivery catheter illustrating radiopaque markers attached to the guidewire tube.

FIGS. 7A-7E are side cut-away views of the stent delivery catheter of the invention positioned in a vessel with the stent segments of FIGS. 5A-5B, illustrating various steps of delivering a prosthesis according to the method of the invention.

FIG. 13 is a side view of a pusher tube.

FIG. 13A is a cross-sectional view of the pusher tube of FIG. 13 taken at line A-A.

DETAILED DESCRIPTION OF THE INVENTION

The present application relates generally to copending U.S. patent application Ser. No. 10/637,713, entitled "Apparatus and Methods for Deployment of Vascular Prostheses," filed Aug. 8, 2003, which application is hereby incorporated by reference.

Figure 1:
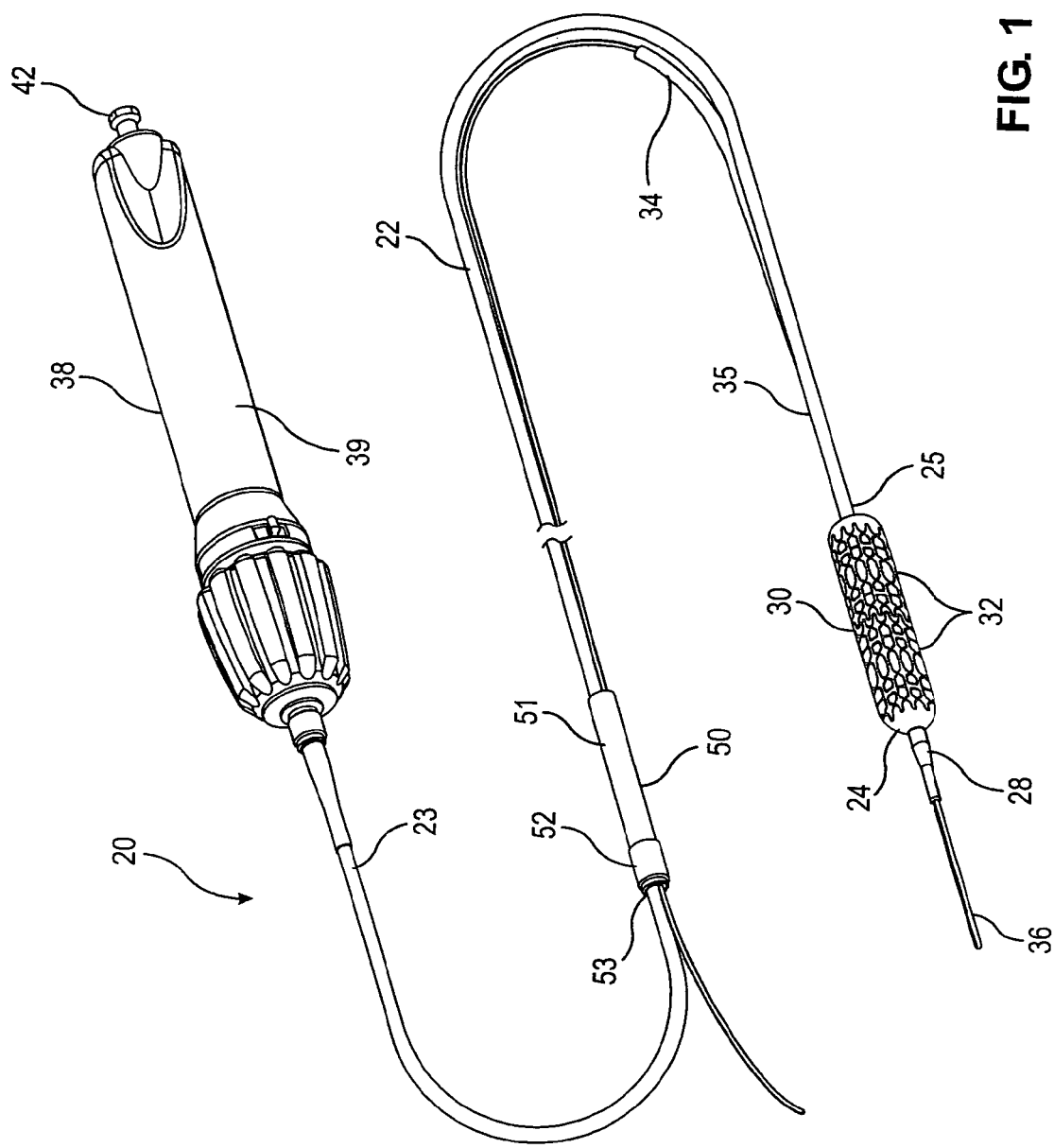
FIG. 1 is a perspective view of a stent delivery catheter according to the invention with sheath retracted and expandable member inflated.

A first embodiment of a stent delivery catheter according to present invention is illustrated in FIG. 1. Stent delivery catheter 20 includes a catheter body 22 comprising an outer sheath 25 slidably disposed over an inner shaft 27 (not shown in FIG. 1). An expandable member 24, preferably an inflatable balloon (shown in an inflated configuration), is mounted to inner shaft 27 and is exposed by retracting sheath 25 relative to inner shaft 27. A tapered nosecone 28, composed of a soft elastomeric material to reduce trauma to the vessel during advancement of the device, is mounted distally of expandable member 24. A stent 30, which preferably comprises a plurality of separate or separable stent segments 32, is disposed on expandable member 24 for expansion therewith. A guidewire tube 34 is slidably positioned through a guidewire tube exit port 35 in sheath 25 proximal to expandable member 24. A guidewire 36 is positioned slidably through guidewire tube 34, expandable member 24, and nosecone 28 and extends distally thereof.

A handle 38 is attached to a proximal end 23 of the sheath 25. The handle 38 performs several functions, including operating and controlling the catheter body 22 and the components included in the catheter body. Various embodiments of a preferred handle and additional details concerning its structure and operation are described in co-pending U.S. patent application Ser. No. 11/148,713 filed Jun. 8, 2005, U.S. Pat. Pub. No. 2006/0282150 A1), entitled "Devices and Methods for Operating and Controlling Interventional Apparatus," which application is hereby incorporated herein by reference.

Embodiments of another preferred handle and details concerning its structure and operation are described in co-pending U.S. application Ser. No. 10/746,466, filed Dec. 23, 2003 (U.S. Pat. No. 7,326,236), entitled "Devices and Methods For Controlling and indicating the Length of an interventional Element," which application is also hereby incorporated herein by reference.

The handle 38 includes a housing 39 that encloses the internal components of the handle. The inner shaft 27 is preferably fixed to the handle, while the outer sheath 25 is able to be retracted and advanced relative to the handle 38. An adaptor 42 is attached to the handle 38 at its proximal end, and is fluidly coupled to the inner shaft 27 in the interior of the housing of the handle 38. The adaptor 42 is configured to be fluidly coupled to an inflation device, which may be any commercially available balloon inflation device such as those sold under the trade name "Indeflator™", available from Guidant Corp. of Santa Clara, Calif. The adaptor is in fluid communication with the expandable member 24 via an inflation lumen in the inner shaft 27 to enable inflation of the expandable member 24.

The outer sheath 25 and guidewire 36 each extend through a slider assembly 50 located on the catheter body 22 at a point between its proximal and distal ends. The slider assembly 50 is adapted for insertion into and sealing within a hemostatic valve, such as on an introducer sheath or guiding catheter, while allowing relative movement of the outer sheath 25 relative to slider assembly 50. The slider assembly 50 includes a slider tube 51, a slider body 52, and a slider cap 53. These components are illustrated in greater detail in FIGS. 16-19.

Figure 16:
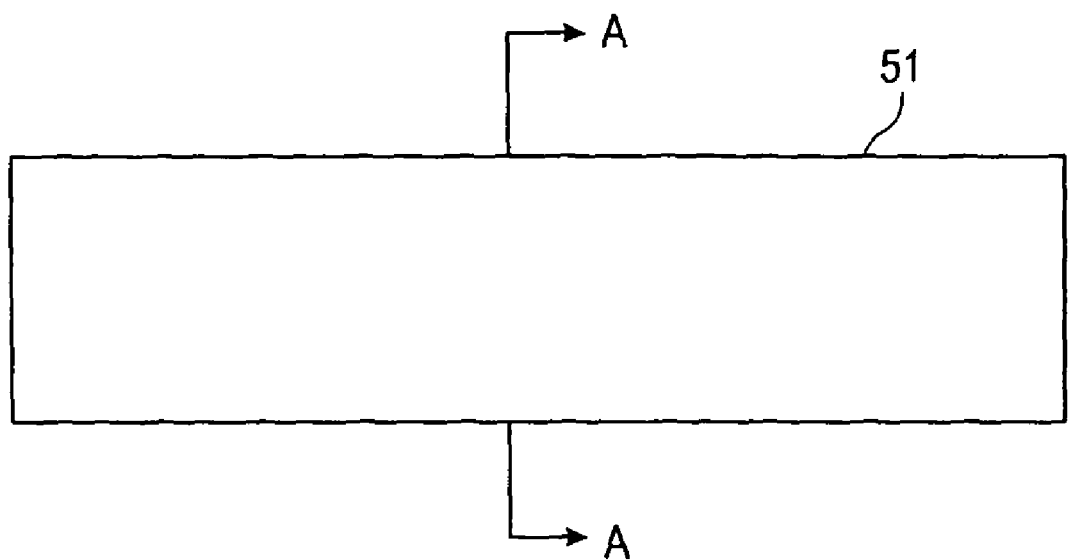
FIG. 16 is a side view of a slider tube.
Figure 16A:
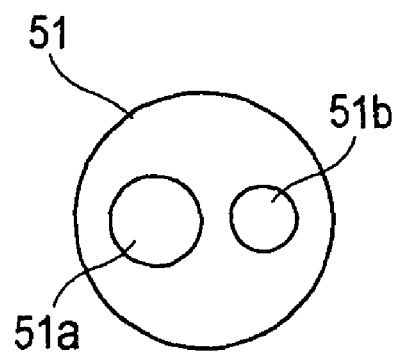
FIG. 16A is a cross-sectional view of the slider tube of FIG. 16 taken at line A-A.
Figure 17B:
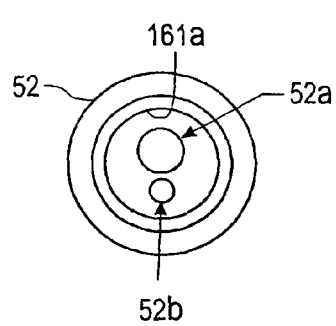
FIG. 17B is an end view of the slider body of FIG. 17.
Figure 17:
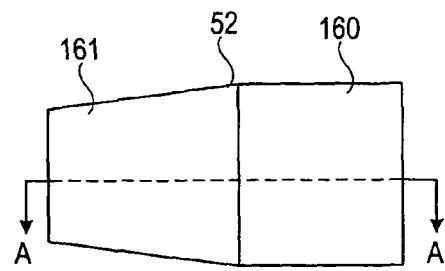
FIG. 17 is a side view of a slider body.
Figure 17A:
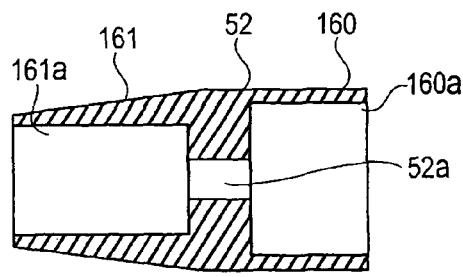
FIG. 17A is a cross-sectional view of the slider body of FIG. 17 taken at line A-A.

In particular, FIGS. 16 and 16A show the slider tube 51, which comprises an elongated cylindrical member having a first through-hole 51a and a second through-hole 51b. The first through-hole 51a has a size to provide a slidable passageway for the catheter body 22, whereas the second through-hole 51b has a size to provide a slidable passageway for the guidewire 34. The slider tube 51 is preferably formed from a polymeric material, such as PTFE, FEP, polyimide, nylon, or Pebax. The slider body 52 is illustrated in FIGS. 17 and 17A-B. The slider body 52 is also an elongated member having a cylindrical section 160 and a tapered section 161. The tapered section 161 has an internal recess 161a that has an interior diameter that provides a snug fit with the external surface of the slider tube 51. The cylindrical section 160 has an internal recess 160a that has an interior diameter that provides a snug fit with the external surface of the slider cap 53. The slider body 52 also includes a first through-hole 52a sized to allow slidable passage of the catheter body 22, and a second through-hole 52b sized to allow passage of the guidewire 34. The slider body is preferably formed from a resilient, relatively incompressible material, such as polycarbonate, and has an exterior surface adapted for being clamped and sealed within a hemostasis valve, preferably being smooth and cylindrical in shape. The slider cap 53 is a relatively short cylindrical member having a first through-hole 53a sized to allow slidable passage of the catheter body 22, and a second through-hole sized to allow slidable passage of the guidewire 34. The slider cap 53 has a size that provides a snug fit with the internal recess 160a of the cylindrical section 160 of the slider body. The slider cap 53 is also preferably formed of a resilient, relatively incompressible material, such as polycarbonate.

Figure 19:
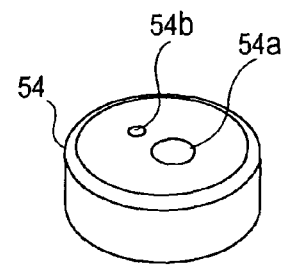
FIG. 19 is a perspective view of a slider seal.
Figure 18B:
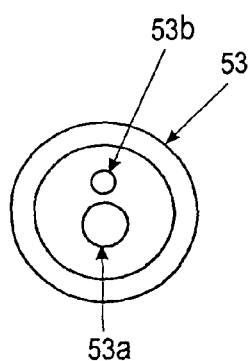
FIG. 18B is an end view of the slider cap of FIG. 18A.
Figure 18A:
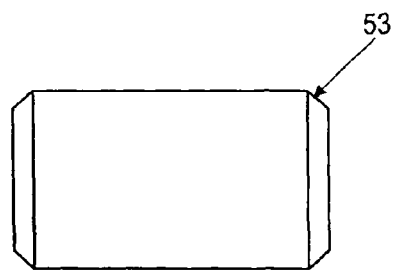
FIG. 18A is a side view of a slider cap.

A slider seal 54 is illustrated in FIG. 19. The slider seal is a short, disc-shaped member having a size adapted to fit snugly within the internal recess 160a of the cylindrical section 160 of the slider body. The slider seal 54 includes a first through-hole 54a sized to allow fluidly sealed, slidable passage of the catheter body 22, and a second through-hole 54b sized to allow fluidly sealed, slidable passage of the guidewire 34. The slider seal is preferably formed of a pliable, resilient material, such as a polymeric material or a silicone compound that is capable of providing a fluid-tight seal with the sheath and guidewire while allowing slidable movement thereof.

The slider assembly 50 is constructed by installing the proximal end of the slider tube 51 into the internal recess 161a of the tapered portion 161 of the slider body, taking care to align the first and second through-holes of each member appropriately. The slider seal 54 is installed in the internal recess 160a of the cylindrical portion 160 of the slider body, and the slider cap 53 is placed over the slider seal 54 within the internal recess 160a, again taking care to ensure that the first and second through-holes of each component are properly aligned. The components are then bonded together by heating or by use of adhesives or other suitable means. The completed slider assembly 50 is then placed over the catheter body 22 and the guidewire 34 as shown in FIG. 1.

Referring now to FIGS. 2A-2B, 3 and 4, which show a distal portion of the stent delivery catheter in cross-section, it may be seen that sheath 25 may be extended up to nosecone 28 to fully surround expandable member 24 and stent segments 32. A garage 55 is attached to the outer sheath 25 at the distal end 57 of the sheath. The garage 55 is a generally cylindrical member having a relatively high circumferential strength such that it is able to prevent the expandable member 24 from inflating when the garage is extended over the inflatable member 24. The garage 55 preferably has a length at least as long as one of the stent segments 32 carried by the catheter, but preferably less than the combined length of two such stent segments. The garage 55 is shown in more detail in FIGS. 9-11, and is described more fully below. A radiopaque marker 56 is preferably formed integrally with or attached to the distal end of the garage 55 to facilitate visualization of the position of the sheath 25 using fluoroscopy. The radiopaque marker 56 may have an axial length selected to provide a visual reference for determining the appropriate distance for stent segment separation, e.g., 2-4 mm, as described below.

The outer sheath 25 further includes a valve member 58 within the garage 55 preferably spaced proximally from the distal end 57 a distance equal to, slightly larger than, or slightly smaller than the length of one of the stent segments 32. For example, in a preferred embodiment, each stent segment 32 has a length of about 4 mm, and the valve member 53 is located approximately 5 mm from the distal end 57 of the sheath or the distal end of the garage member 55. In other embodiments, the valve member 58 may be spaced from the distal end 57 a distance equal to about ¼-¾ of the length of one stent segment 32, more preferably one-half the length of one stent segment 32. Valve member 58 preferably comprises a necked-down circumferential waist or inwardly extending ring-shaped flange 60 configured to frictionally engage stent segments 32 and thereby restrict the sliding movement of stent segments 32 distally relative to sheath 25. Flange 60 may be a polymeric or metallic material integrally formed with sheath 25 or, preferably, with the garage 55, or a separate annular member bonded or otherwise mounted to the interior of the sheath 25 or the garage 55. The geometry of flange 60 may be toroidal with circular cross-section (like an O-ring) or it may have another cross-sectional shape such as triangular, trapezoidal, or pyramidal. Preferably flange 60 is a polymer such as silicone or urethane sufficiently soft, compliant, and resilient to provide frictional engagement with stent segments 32 without damaging the stent segment or any coating deposited thereon. Valve member 58 will extend radially inwardly a sufficient distance to engage the exterior of stent segments 32 with sufficient force to allow the line of stent segments 32 remaining within sheath 25 to be retracted proximally with sheath 25 so as to create spacing relative to those stent segments disposed distally of sheath 25 for deployment. At the same time, valve member 58 should not exert so much force that it removes or damages the coating on the exterior surface of stent segments 32 as sheath 25 is retracted relative to the stent segments to expose a desired number of stem segments 32. In a preferred embodiment, stem segments 32 have an outer diameter of about 0.040-0.050 in. (including coating) and sheath 25 and garage 55 have inner diameter 0.041-0.051 in. so as to provide clearance of about 0.001 in. with stein segments 32. Valve member 58 has a preferred inner diameter about 0.003-0.008 in. less than that of garage 55, or about 0.033-0.048", so as to provide an interference fit with stent segments 32. Valve member 58 will preferably exert a force of about 0.5-5 lbs. on a stent segment 32 positioned within it. Various embodiments of valve member 58 are described in copending application Ser. No. 10/412,714, Filed Apr. 10, 2003 (U.S. Pat. No. 7,137,993), which is incorporated herein by reference.

Figure 9:
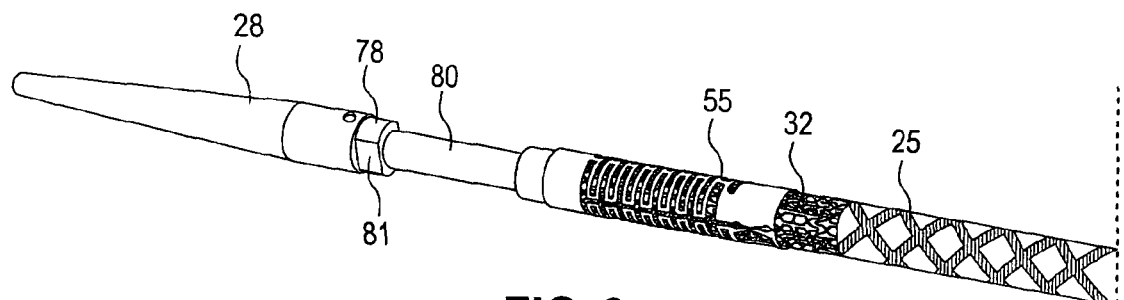
FIG. 9 is a perspective view of the distal portion of the stent delivery catheter of the invention with a portion of the outer sheath stripped away to reveal a garage member.
Figure 10:
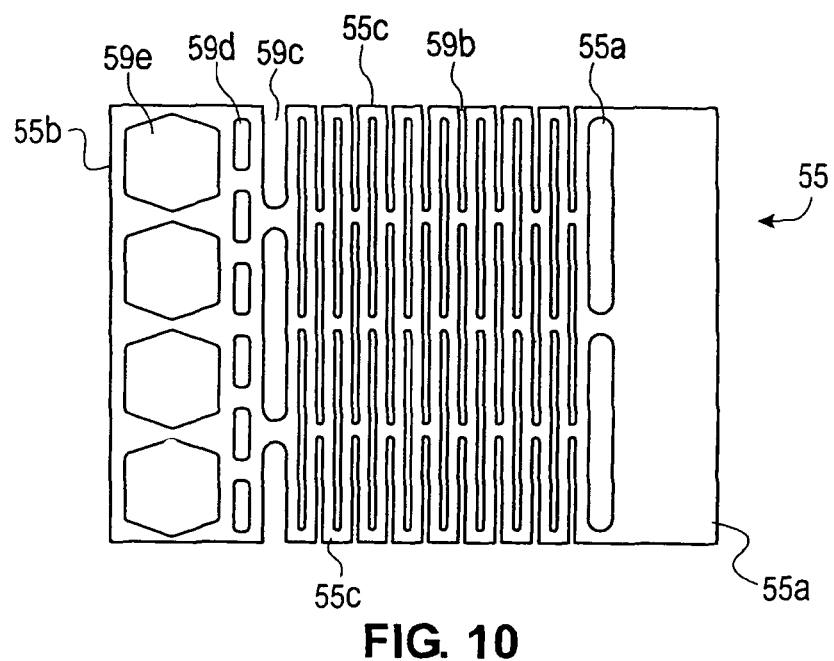
FIG. 10 is a planar view of a garage member.
Figure 11:
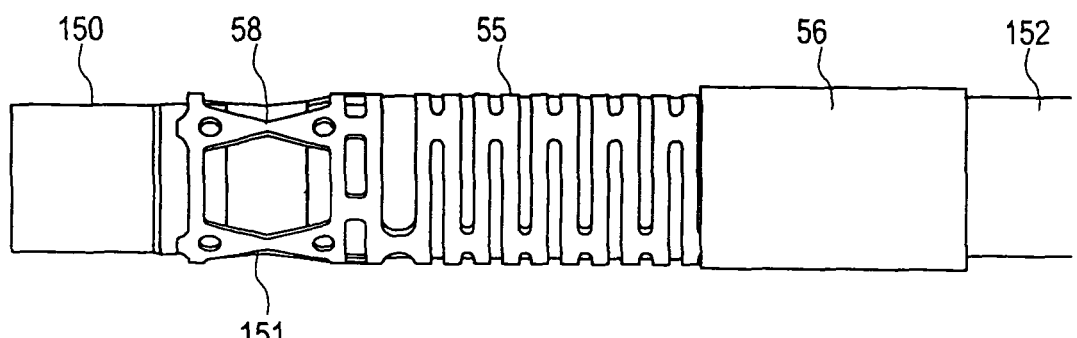
FIG. 11 is a side view of a garage member attached to a pair of mandrels.

FIGS. 9-11 illustrate the garage 55, the radiopaque marker 56, and the valve member 58 in greater detail. The garage 55 is a cylindrical member that is preferably mounted to the distal end of the outer sheath 25. FIG. 9 illustrates the garage 55 as it is oriented surrounding the stent segments 32 aligned over the inner shaft. The distal portion of the outer sheath 25 is shown stripped away in FIG. 9 to reveal the orientation of the garage 55. The cylindrical garage 55 is preferably formed of a metallic, polymeric, or other material and in a geometry to provide high radial strength and high axial flexibility. Superelastic alloys are preferred materials. A preferred garage material is Nitinol.

The structure of the garage 55 is illustrated in FIG. 10, in which the garage 55 is shown in a planar form for clarity. The garage 55 is preferably laser cut from a tube, but may also be cut, stamped, or otherwise formed from a sheet of material.

A number of cut-outs or windows 59 are preferably formed in the body of the garage to increase its axial flexibility. Preferably, the garage 55 is constructed in a manner of and of materials that allow it to bend about a transverse axis. Although the number, size, and shape of the cut-outs 59 may vary, the illustrated embodiment includes a preferred form. The distal end 55a of the garage 55 is provided with no cut-outs in order to provide the greatest radial strength at the distal end of the sheath, where the restraining force against the expandable member 24 is the greatest. A pair of first cut-outs 59a having oval or rectangular shape are formed a short distance from the distal end 55a of the garage, the pair of first cut-outs 59a being aligned circumferentially around the periphery of the garage. A series of narrow second cut-outs 59b having a linear or slot-like shape are formed over the central portion of the body of the garage 55. Preferably, the second cut-outs 59b are provided in a staggered formation to provide greater axial flexibility over the central portion of the garage. A series of third cut-outs 59c are located just proximally of the central portion of the garage. The third cut-outs 59c are of a similar size and shape to the first cut-outs 59a, but are circumferentially staggered from the first cut-outs 59a. A series of fourth rectangular or oval-shaped cut-outs 59d are located just proximally of the third cut-outs, and are both narrower and shorter than the third cut-outs 59c. Finally, a series of fifth cut-outs 59e having a hexagonal shape are provided near the proximal end 55b of the garage. Each of the fifth cut-outs 59e is substantially wider (i.e., greater longitudinal length) than the other cut-outs 59a-d. As noted below, the position of the fifth cut-outs corresponds with the location of the valve member 58.

Turning to FIG. 11, the garage 55 is shown supported on a proximal mandrel 150 and a distal mandrel 152 to facilitate attachment of the valve member 58 and sheath 25 thereto. The proximal mandrel is provided with an indentation or concavity adapted to receive and retain the valve member 58 in place for the purpose of attaching the valve member 58 to the garage 55 and outer sheath 25. The radiopaque marker 56 may be placed over the distal end 55a of the garage 55. After the foregoing components have been properly aligned, the outer sheath 25 is attached to the proximal end 55b of garage 55, preferably by placing a piece of shrink tubing over the garage and distal end of the outer sheath and heating the assembly. The garage 55 is thereby covered with a polymer material about its exterior. Of course various other attachment techniques may be used including heat treatment, adhesives, or other methods known to those skilled in the art.

As thus described, the sheath 25 has a distal extremity 62 configured to surround expandable member 24 and stent segments 32 disposed thereon when in an unexpanded configuration. Distal extremity 62 extends proximally to a junction 63, preferably aligned with the location of guidewire tube exit port 35, where distal extremity 62 is joined to a proximal extremity 64 that extends proximally to handle 38 (see FIG. 1). In a preferred embodiment, distal extremity 62 has a length of about 15-35 cm and proximal extremity 64 as a length of about 100-125 cm. Proximal extremity 64 may be constructed of a variety of biocompatible polymers, metals, or polymer/metal composites, preferably being stainless steel or Nitinol. Distal extremity 62 may be a polymer such as PTFE, FEP, polyimide, nylon, or Pebax, or combinations of any of these materials. In a preferred form, the distal extremity 62 comprises a composite of nylon, PTFE, and polyimide. The distal extremity is preferably reinforced with a metallic or polymeric braid to resist radial expansion when expandable member 24 is expanded. Sheath 25 may further have a liner surrounding its interior of low friction material such as PTFE to facilitate relative motion of sheath 25, stent segments 32, and pusher tube 86.

Preferably, proximal extremity 64 has a smaller transverse dimension than distal extremity 62 to accommodate the added width of guidewire tube 34 within the vessel lumen, as well as to maximize flexibility and minimize profile. In one embodiment, shown in FIG. 3, distal extremity 62 is a tubular member having a first outer diameter, preferably about 1.0-1.5 mm, and proximal extremity 64 is a tubular member having a second, smaller outer diameter, preferably about 0.7-1.0 mm. At the junction of proximal extremity 64 with distal extremity 62, a proximally-facing crescent-shaped opening 65 is formed between the two tubular members that creates guidewire tube exit port 35. Excess space within crescent-shaped opening 65 may be filled with a filler material such as adhesive or a polymeric material (e.g., Pebax).

In an alternative embodiment (not shown), a hole is formed in the sidewall of distal extremity 62 or proximal extremity 64 to create guidewire tube exit port 35. Proximally of guidewire tube exit port 35, the wall of sheath 25 adjacent to guidewire tube 34 is flattened or collapsible inwardly thereby reducing the transverse dimension of sheath 25 to accommodate the width of guidewire tube 34.

Guidewire tube 34 is slidably positioned through guidewire tube exit port 35. The guidewire tube exit port 35 may be configured to provide a total or partial fluid seal around the periphery of guidewire tube 34 to limit blood flow into the interior of sheath 25 and to limit leakage of saline (or other flushing fluid) out of sheath 25. This may be accomplished by sizing guidewire tube exit port 35 appropriately so as to form a fairly tight frictional seal around guidewire tube 34 while still allowing the sliding motion thereof relative to sheath 25. Alternatively an annular sealing ring may be mounted in guidewire tube exit port 35 to provide the desired seal. Preferably, however, the guidewire tube exit port 35 is not totally fluid sealed, so as to provide a slight leakage or fluid flow to provide the ability to flush the distal extremity 62 of the catheter.

Guidewire tube exit port 35 will be positioned to provide optimal tracking of stent delivery catheter 20 through the vasculature and maximizing the ease with which the catheter can be inserted onto and removed from a guidewire to facilitate catheter exchanges. Usually, guidewire tube exit port 35 will be positioned at a location proximal to expandable member 24 when sheath 25 is extended fully distally up to nosecone 28, but a distance of no more than one-half the length of sheath 25 from distal end 57. In preferred embodiments for coronary applications, guidewire tube exit port 35 is spaced proximally a distance of about 20-35 cm from the distal end 57 of sheath 25.

Guidewire tube 34 should extend proximally from guidewire tube exit port 35 a distance at least as long as the longest possible stent that may be deployed, e.g., 30-200 mm depending upon the application, to allow for retraction of sheath 25 that distance while retaining a portion of guidewire tube 34 external to sheath 25. Preferably the guidewire tube 34 extends proximally a distance of about 35 to about 70 mm from the guidewire tube exit port 35 when sheath 25 is in a fully distal position, with the proximal end thereof disposed a distance of about 23-50 cm from the distal tip of nosecone 28. Where stent delivery catheter 20 is to be positioned through a guiding catheter, the proximal end of guidewire tube 34 will preferably be positioned so as to be within the guiding catheter when expandable member 24 is positioned at the target site for stent deployment. Guidewire tube 34 is preferably a highly flexible polymer such as PTFE, FEP, polyimide, or Pebax, and may optionally have a metal or polymer braid or fiber embedded in it to increase kink-resistance and tensile strength.

Inner shaft 27 forms an inflation lumen 66 that is in communication with interior of expandable member 24. The inner shaft 27 may be formed of a polymer material such as PTFE, FEP, polyimide, or Pebax, or the inner shaft 27 may be a metal such as stainless steel or Nitinol.

Expandable member 24 has an expandable balloon member 70 that is joined to a non-expandable tubular leg 72. Expandable balloon member 70 is a semi-compliant polymer such as Pebax, polyurethane, or Nylon. Non-compliant, fully elastic, or other materials such as PTFE may also be used. Preferably, the compliance of the balloon member allows the expanded diameter of balloon member 70 to be adjusted by selecting the appropriate inflation pressure delivered thereto, thereby allowing customization of the deployed diameter of stent segments 32. For example, in one embodiment, balloon member 70 may be inflated to a pressure of between about 5 and about 12 atmospheres, allowing the deployed stent diameter to be adjusted from about 2.0 mm to 4.0 mm. Of course, larger and smaller stent diameters are also possible by utilizing appropriate stent geometry and applying suitable inflation pressures. Tubular leg 72 is preferably a polymer such as polyimide, PTFE, FEP, polyurethane, or Pebax and may optionally be reinforced with a metal or polymer braid or metal or polymer fibers. Tubular leg 72 has an open proximal end 74 through which guidewire tube 34 extends. Proximal end 74 of tubular leg 72 is fixed to distal end 68 of inner shaft 27 and to guidewire tube 34, forming a fluid-tight seal. Guidewire tube 34 passes through the interior of balloon member 70 and is mounted to nosecone 28, thereby providing a passage through the distal portion of catheter body 22 through which guidewire 36 may pass. Balloon member 70 has a distal end 76 that extends over an annular stop 78, which is mounted to the distal end of guidewire tube 34 and/or nosecone 28. Distal end 76 of balloon member 70 may be bonded to stop 78, guidewire tube 34, and/or nosecone 28. The stop 78 has a size and shape selected to engage stent segment 32 and provide a stop against which stent segments 32 can be located in the ideal deployment position without being pushed beyond the distal end of balloon member 70. Additional details concerning stent stops suitable for use in the devices and methods described herein are disclosed in U.S. patent application Ser. No. 10/884,616, filed Jul. 2, 2004, which is hereby incorporated by reference herein.

Figure 9A:
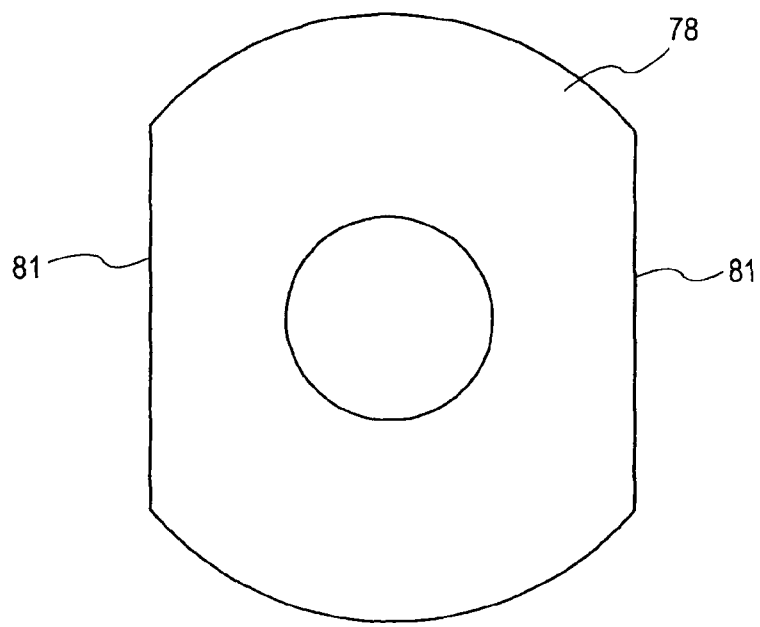
FIG. 9A is an end view of a stop member.

Preferably, the stop 78 has a partial cylindrical shape, rather than a full cylindrical shape, as a relief to reduce interference with garage 55. For example, FIGS. 9 and 9A illustrate the stop 78 having a flat portion 81 formed on the opposed lateral surfaces of the stop 78. A similar flat portion may be formed on the upper and lower sides of the stop 78. The provision of flat portions on the stop 78 allows the stop 78 to limit distal movement of the stent segments 32, while reducing interference between stop 78 and the interior of garage 55.

Optionally, within the interior of balloon member 70 an annular base member 80 is mounted to guidewire tube 34 and has a diameter selected to urge balloon member 70 against stent segments 32 in their unexpanded configuration, thereby providing frictional engagement with stent segments 32. This helps to limit unintended sliding movement of stent segments 32 on balloon member 70. Base member 80 may be made of a soft elastomer, foam, or other compressible material.

Figure 12A:
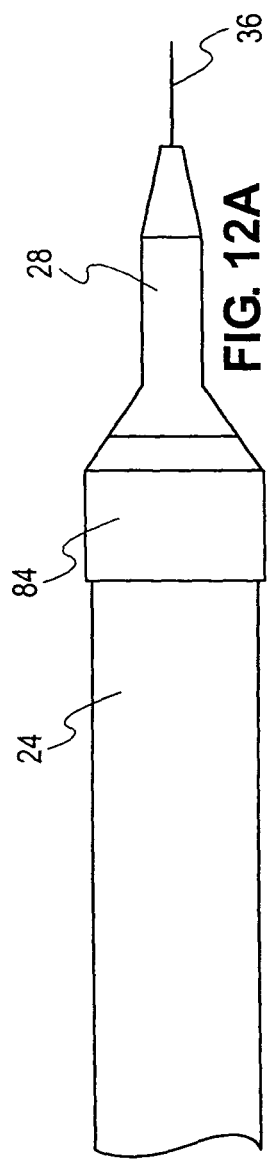
FIG. 12A is a side view of an expandable member in its expanded state.
Figure 12B:
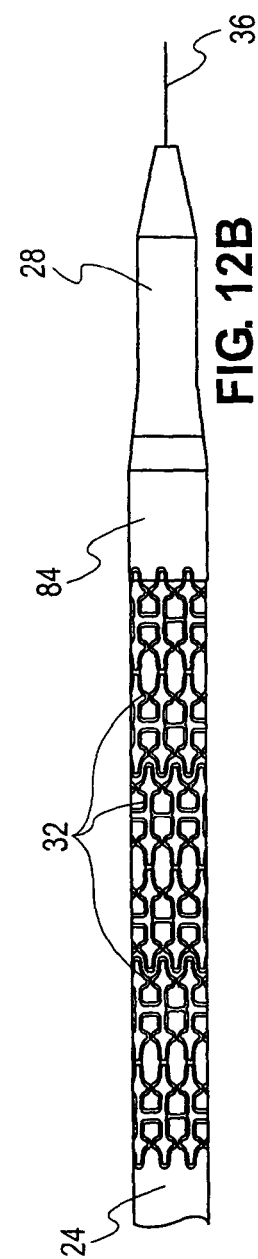
FIG. 12B is a side view of an expandable member in its contracted state and having a plurality of stent segments thereon.

An additional option or alternative structure for limiting unintended sliding or movement of the stent segments is the provision on the distal exterior portion of the expandable member 24 of a layer of material 84 having a high coefficient of friction so as to frictionally engage the stent segments 32. See FIGS. 12A-C. For example, a layer of a polymeric material 84, such as polyurethane, will prevent the stent segments 32 from sliding off the distal end of the balloon, and will cause the stent segments 32 to stop in the desired location near the distal end of the expandable member 24. The layer of material 84 is preferably formed over the entire circumference of the distal end of the expandable member 24, as shown in the Figures, but may alternatively be placed only at spaced intervals around the periphery. The material layer 84 is preferably formed of elastomeric materials and in a manner that allows it to expand and contract as the expandable member 24 expands and contracts. For example, the material layer 84 may be applied by dipping the expandable member 24 in a liquid polymer, by spraying, or by attaching a sheet or tube of material over the expandable member 24 by adhesive or heat treatment. As the stent segments 32 move distally relative to the expandable member 24 in its contracted state, the distal end of the most distal stent segment will come into contact with the layer of material 84 and the friction force encountered by the stent segment 32 will increase. This will inhibit or prevent additional relative movement between the stent segment 32 and the expandable member 24. In addition, the increased frictional resistance may serve as a tactile indicator to the user of the position of the stent segment 32 relative to the expandable member 24. Material layer 84 may be of equal thickness along it length, or the thickness of the material layer 84 may gradually increase in the distal direction to provide gradually increasing interference with stent segments 32. Material layer 84 may have an outer surface at the same height as the outer surface of expandable member 24 to provide a smooth transition therebetween, or material layer 84 may be of greater height to provide a step that enhances engagement with stent segments 32.

Figure 12C:
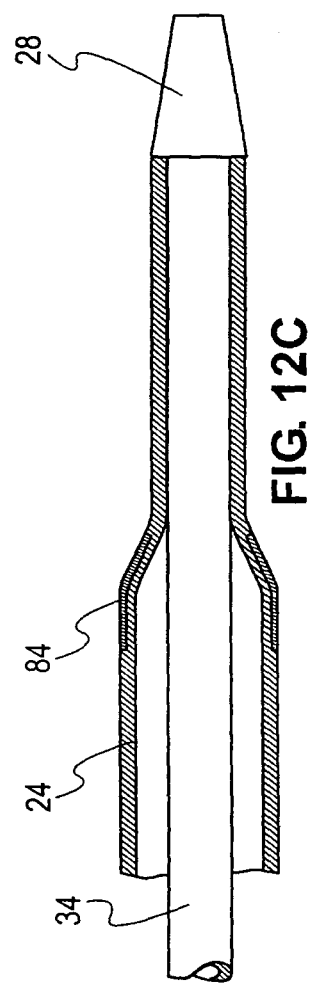
FIG. 12C is a side cross-section of an expandable member according to the invention.

In a preferred embodiment as shown in FIG. 12C, expandable member 24 is molded with a circumferential channel, stepped geometry, and/or with reduced wall thickness near its distal end so as to have a smaller outer diameter in the region where the material layer 84 is to be applied to accommodate the thickness of material layer 84. In this way, the outer wall of the expandable member 24 and material layer 84 will be smooth and continuous without an abrupt change in elevation, allowing stent segments 32 to slide smoothly from the expandable member 24 to the material layer 84. Alternatively, expandable member 24 and/or material layer 84 may have an outer diameter or wall thickness that is stepped outwardly or that gradually increases in the distal direction so as to increase the frictional resistance with stent segments 32. In alternative embodiments, material layer 84 may have surface features such as bumps, ridges, projections, or scales to increase friction against stent segments 32.

Annular radiopaque markers 82 may be mounted to the guidewire tube 34, facilitating visualization of the location of balloon member 70 with fluoroscopy and enabling appropriate positioning of stent segments 32 on balloon member 70. Referring to FIG. 2C, the radiopaque markers 82 are preferably located at regular intervals along the length of the guidewire tube 34. In a particularly preferred form, the radiopaque markers 82 are spaced at intervals that are related to the length of individual stent segments 32, such as being at intervals equal to the stent segment lengths, one-half of stent segment length, double stent segment length, or the like. Stated otherwise, the distance between the distal ends of adjacent markers 82 (or the proximal ends of adjacent markers 82, or the mid-points of adjacent markers 82, etc.) are provided equal to the stent segment lengths, one-half of stent segments length, double stent segment length, or the like. Locating multiple radiopaque markers 82 on the guidewire tube 34 at regularly spaced intervals provides a visual reference for determining the location and number of stent segments 32 on expandable member 24 under fluoroscopy. Further, the length of expandable member 24 and stent segments 32 exposed during retraction of sheath 25 may be determined under fluoroscopy by observing the position of marker 56 on garage member 55 relative to marker(s) 82 on guidewire tube 34. Alternatively, only a single marker 82 at or near the distal end of balloon member 70 may be used, or markers may be placed at both the distal end and proximal end of the base member 80, or markers may be placed at other locations on nosecone 28, guidewire tube 34, or inner shaft 27. Such markers may be made of various radiopaque materials such as platinum/iridium, tantalum, gold, and other materials.

Stent segments 32 are slidably positioned over balloon member 70. Depending upon the number of stent segments 32 loaded in stent delivery catheter 20, stent segments 32 may be positioned over both balloon member 70 and tubular leg 72. In an exemplary embodiment, each stent segment is about 2-20 mm in length, more preferably 2-8 mm in length, and 3-50 stent segments may be positioned end-to-end in a line over balloon member 70 and tubular leg 72. Stent segments 32 preferably are in direct contact with each other, but alternatively separate spacing elements may be disposed between adjacent stent segments, the spacing elements being movable with the stent segments along balloon member 70. Such spacing elements may be plastically deformable or self-expanding so as to be deployable with stent segments 32 into the vessel, but alternatively could be configured to remain on balloon member 70 following stent deployment; for example, such spacing elements could comprise elastic rings which elastically expand with balloon member 70 and resiliently return to their unexpanded shape when balloon member 70 is deflated. The spacing elements could be pushed to the distal end of balloon member 70 against stop 78 as additional stent segments 32 are advanced distally.

Stent segments 32 are preferably a malleable metal so as to be plastically deformable by expandable member 24 as they are expanded to the desired diameter in the vessel. Alternatively, stent segments 32 may be formed of an elastic or super elastic shape memory material such as Nitinol so as to self-expand upon release into the vessel by retraction of sheath 25. Stent segments 32 may also be composed of polymers or other suitable biocompatible materials including bioabsorbable or bioerodable materials. In self-expanding embodiments, expandable member 24 may be eliminated or may be used for predilatation of a lesion prior to stent deployment or for augmenting the expansion of the self-expanding stent segments.

In preferred embodiments, stent segments 32 are coated with a drug that inhibits restenosis, such as Rapamycin, Paclitaxel, Biolimus A9 (available from BioSensors International), analogs, prodrugs, or derivatives of the foregoing, or other suitable agent, preferably carried in a durable or bioerodable polymeric or other suitable carrier material. Alternatively, stent segments 32 may be coated with other types of drugs and therapeutic materials such as antibiotics, thrombolytics, anti-thrombotics, anti-inflammatories, cytotoxic agents, antiproliferative agents, vasodilators, gene therapy agents, radioactive agents, immunosuppressants, and chemotherapeutics. Several preferred therapeutic materials are described in U.S. Published Patent Application No. 2005/0038505, entitled "Drug-Delivery Endovascular Stent and Method of Forming the Same," filed Sep. 20, 2004, which application is hereby incorporated by reference herein. Such materials may be coated over all or a portion of the surface of stent segments 32, or stent segments 32 may include apertures, holes, channels, pores, or other features in which such materials may be deposited. Methods for coating stent segments 32 are described in the foregoing published patent application. Various other coating methods known in the art may also be used, including syringe application, spraying, dipping, inkjet printing-type technology, and the like.

Stent segments 32 may have a variety of configurations, including those described in copending application Ser. No. 10/738,666, filed Dec. 16, 2003 (U.S. Pat. Pub. No. 2004/0186551 A1), which is incorporated herein by reference. Other preferred stent configurations are described below. Stent segments 32 are preferably completely separate from one another without any interconnections, but alternatively may have couplings between two or more adjacent segments which permit flexion between the segments. As a further alternative, one or more adjacent stent segments may be connected by separable or frangible couplings that are separated prior to or upon deployment, as described in co-pending application Ser. No. 10/306,813, filed Nov. 27, 2002 (U.S. Pat. Pub. No. 2003/0135266 A1), which is incorporated herein by reference.

Figure 2A:
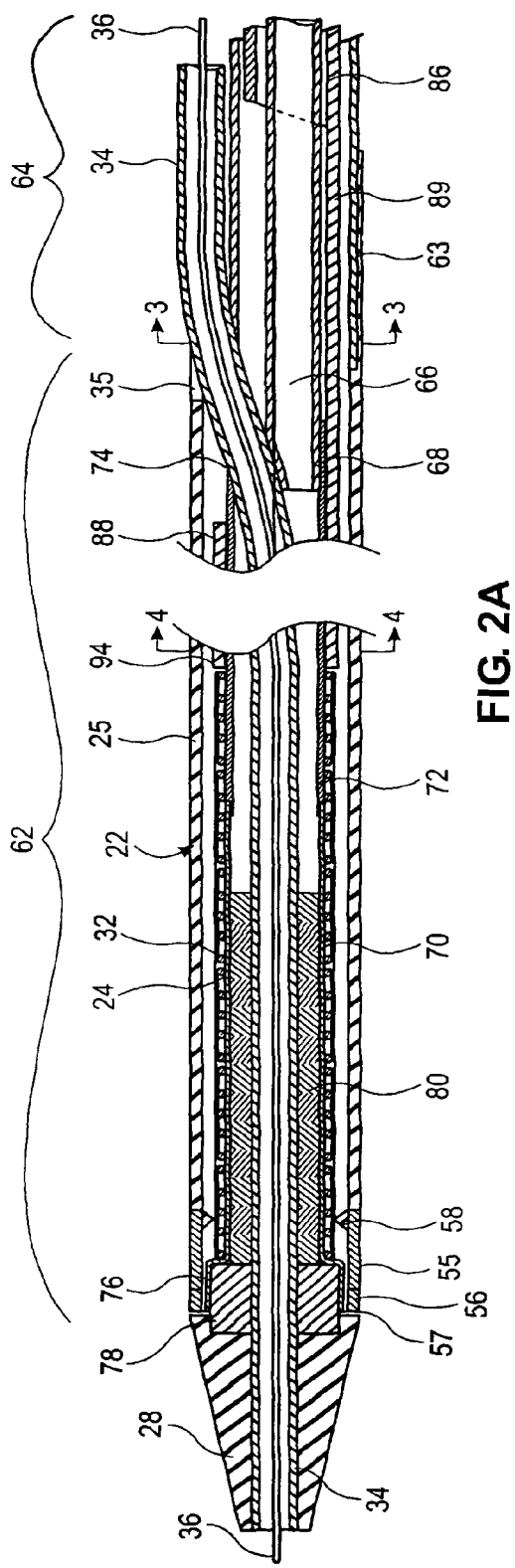
FIG. 2A is a side cross-section of a distal portion of the stent delivery catheter of FIG. 1 with expandable member deflated and sheath advanced distally.
Figure 4:
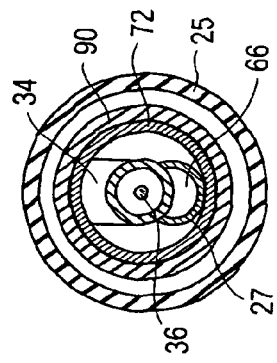
FIG. 4 is a transverse cross-section through line 4-4 of FIG. 2A.
Figure 3:
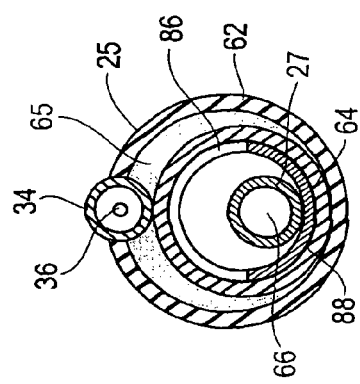
FIG. 3 is a transverse cross-section through line 3-3 of FIG. 2A.
Figure 2B:
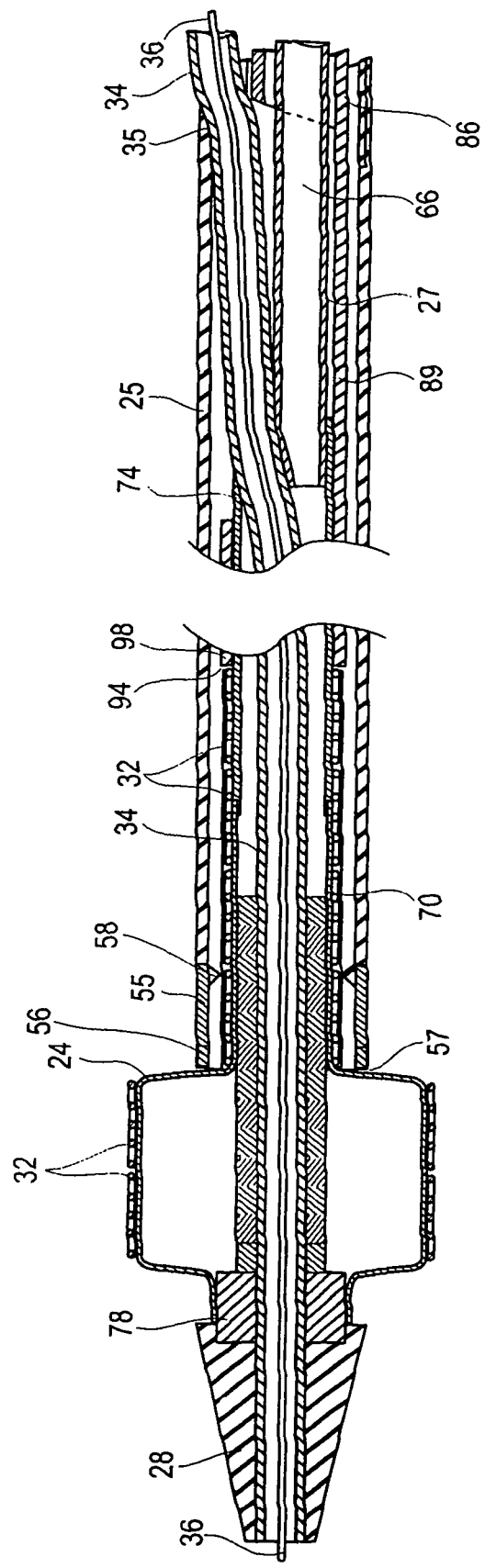
FIG. 2B is a side cross-section of a distal portion of the stent delivery catheter of FIG. 1 with expandable member inflated and sheath retracted.

A pusher tube 86 is slidably disposed over inner shaft 27. The structure of the pusher tube 86 is illustrated in FIG. 13, and its location within the catheter body 22 is best shown in FIGS. 2A-B. The pusher tube 86 contains three primary sections, a distal extension 88, a ribbon portion 89, and a proximal portion 90. The proximal portion 90 extends from the handle 38 over the inner shaft 27 and to the ribbon portion 89. The proximal portion 90 is preferably formed of a tubular material to provide high column strength but adequate flexibility to extend through the vasculature from an access site to the coronary ostia or other target vascular region. A preferred material is stainless steel hypotube. The ribbon portion 89 of the pusher tube corresponds with the location of the guidewire exit port 35 on the outer sheath 25. The ribbon portion 89 is formed of a partial-tube, see, e.g., FIG. 13A, in order to provide an opening to allow the guidewire tube 34 to pass through to the exit port 35. The proximal portion of the ribbon portion 89 is formed out of the same tubular material that makes up the proximal portion 90 of the pusher tube, e.g., stainless steel hypotube. The proximal portion of the ribbon portion 89 is joined to the distal portion of the ribbon 89, such as by a weld 91 or the ribbon portion and proximal portion may be formed from the same hypotube which is laser cut in the appropriate geometry. The distal extension 88 is preferably formed of a slotted tube of rigid material, such as stainless steel or Nitinol. The slotted tube making up the distal extension 88 includes a number of cylindrical rings 92 interconnected by longitudinal connectors 93, thereby defining a plurality of transverse slots 97 arranged in pairs along the length of the distal extension. Each pair of slots is disposed opposite one another on distal extension 88, thus defining a pair of opposing, longitudinal connectors 93. The longitudinal connectors 93 are flexible so as to be capable of bending around a transverse axis. Each pair of transverse slots 97 is oriented at 90 degrees relative to the adjacent pair of slots 97, so that the pairs of longitudinal connectors 93 alternate between those oriented vertically and those oriented horizontally. This allows distal extension 88 to bend about either a horizontal and vertical transverse axes, thus providing a high degree of flexibility. Of course, the pairs of transverse slots 97 could be oriented at various angles relative to adjacent pairs to provide flexibility about more than two axes. The slots provided in the slotted tube allows the distal extension 88 to be more axially flexible than it would be without the slots, while still retaining high column strength. It is preferable to provide transverse slots 97 and cylindrical rings 92 that each have a width that is approximately the same as the length of a stent segment 32. In addition or alternatively, the transverse slots 97 and cylindrical rings 92 may be spaced apart by a known fraction or multiple of the stent segment length. In this way, a detent mechanism may be provided on the interior surface of the sheath 25, with one or more detents that releasably engage the cylindrical rings 92 formed in the distal extension 88 to provide a tactile feedback based upon the distance that the outer sheath 25 is retracted relative to pusher tube 86. A nesting tip 94 is formed on the distal end of the distal extension 88. The nesting tip preferably includes a plurality of fingers shaped and oriented to engage and interleave with the proximal end of the most proximal stent segment 32. As described elsewhere herein, stent segments 32 preferably have axial extensions or projections on each end which interleave with those on the adjacent stent segment. Tip 94 of pusher tube 86 preferably has a geometry with axial projections similar to or complementary to those of stent segments 32 so as to interleave therewith.

Preferably, the proximal portion 90 of the pusher tube has a diameter that is smaller than the diameter of the distal extension 88. Thus, the stainless steel hypotube material making up the proximal portion 90 of the pusher tube and part of the ribbon portion 89 may have a first diameter, while the slotted tube making up the distal extension 88 and the distal portion of the ribbon 89 may have a second, larger diameter.

As noted above, the slotted tube and the hypotube are preferably joined by a weld 91 formed in the ribbon portion 89.

As best shown in FIGS. 2A-B, the pusher tube 86 extends longitudinally within the outer sheath 25 and over the inner shaft 27 through most of the length of the catheter body 22. The distal extension 88 is slidable over the tubular leg 72 and engages the stent segment 32 at the proximal end of the line of stent segments 32. At its proximal end (not shown), the pusher tube 86 is coupled to an actuator associated with the handle 38 (see FIG. 1). In this way, the pusher tube 86 can be advanced distally relative to inner shaft 27 to urge the stent segments 32 distally over the expandable member 24 (or, alternatively, the pusher tube 86 may be held in position while retracting the expandable member 24 relative to stent segments 32) until the stent segments engage the stop 78. In addition, the pusher tube 86 can be used to hold the stent segments 32 in place on the expandable member 24 while the sheath 25 is retracted to expose a desired number of stent segments 32, as shown in FIG. 2B. As noted above, the proximal portion 90, ribbon portion 89, and distal extension 88 of the pusher tube are preferably constructed of stainless steel, but they may alternatively be constructed of a variety of biocompatible polymers, metals, polymer/metal composites, alloys, or the like.

It can be seen that with sheath 25 retracted a desired distance, expandable member 24 is allowed to expand when inflation fluid is delivered through inflation lumen 66, thereby expanding a desired number of stent segments 32 exposed distally of sheath 25. The remaining portion of expandable member 24 and the remaining stent segments 32 within sheath 25 are constrained from expansion by sheath 25.

FIG. 2B further illustrates that when sheath 25 is retracted relative to expandable member 24, guidewire tube exit port 35 becomes further away from the point at which guidewire 36 exits the proximal end 74 of tubular leg 72, increasing the distance that guidewire 36 must pass within the interior of sheath 25. Advantageously, guidewire tube 34 provides a smooth and continuous passage from the tubular leg 72 through guidewire tube exit port 35, eliminating any problems that might result from changing the alignment of the two. This is particularly important in the present invention where the stent delivery catheter may carry a large number of stent segments 32 and sheath 25 may be retracted a substantial distance relative to expandable member 24, resulting in substantial misalignment of guidewire tube exit port 35 relative to tubular leg 72.

Figure 14A:
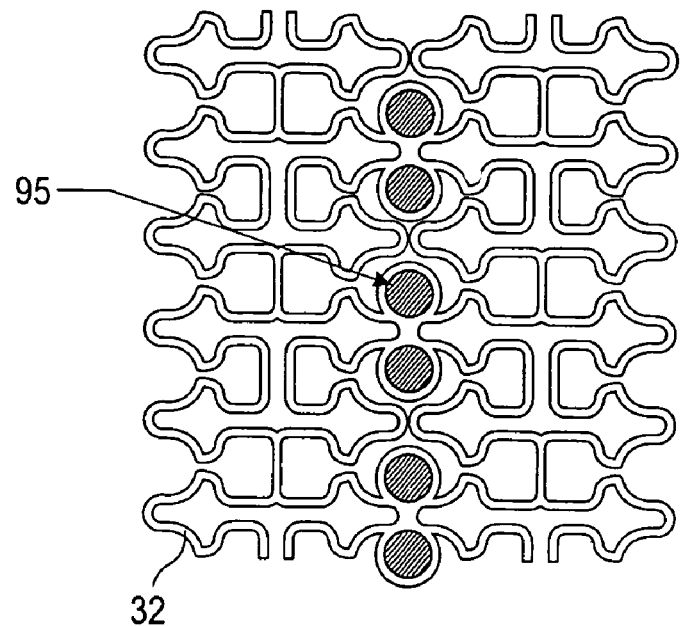
FIGS. 14A-B are side views of a stent segment embodiment having radiopaque markers affixed thereto.
Figure 14B:
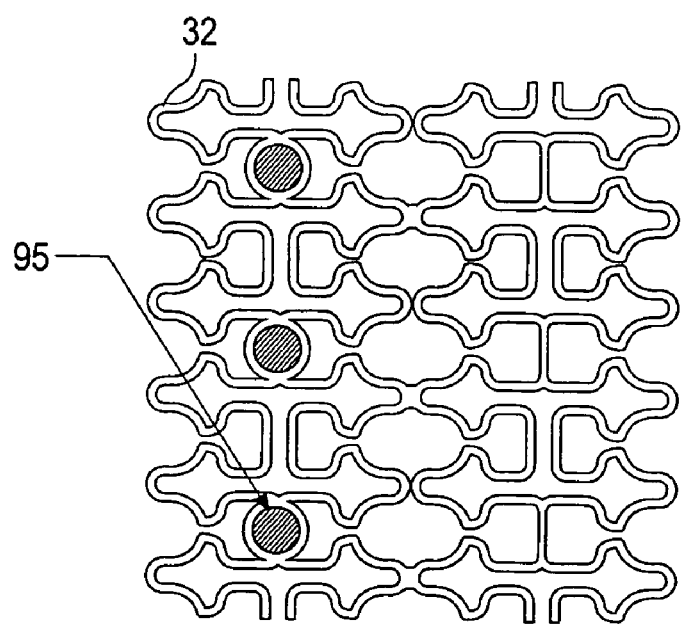
Figure 15A:
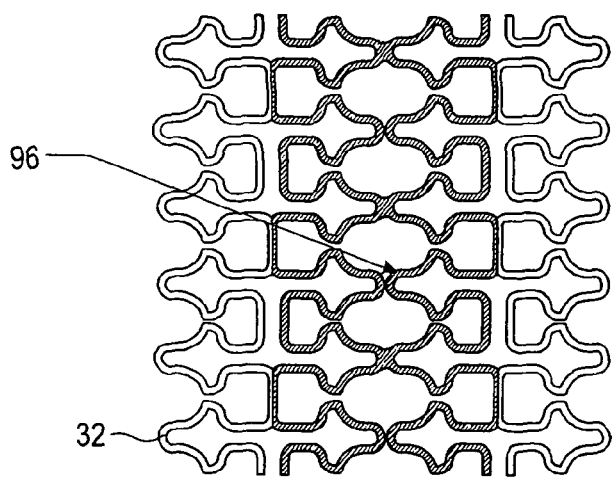
FIGS. 15A-C are side views of stent segment embodiments having radiopaque marker coatings applied thereto.
Figure 15B:
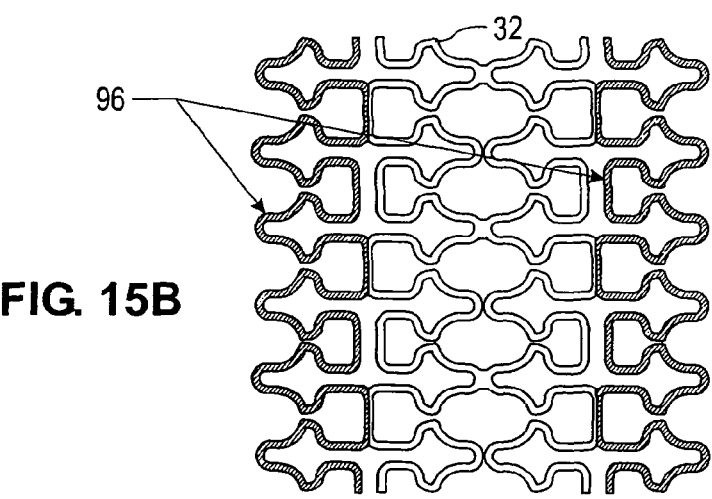
Figure 15C:
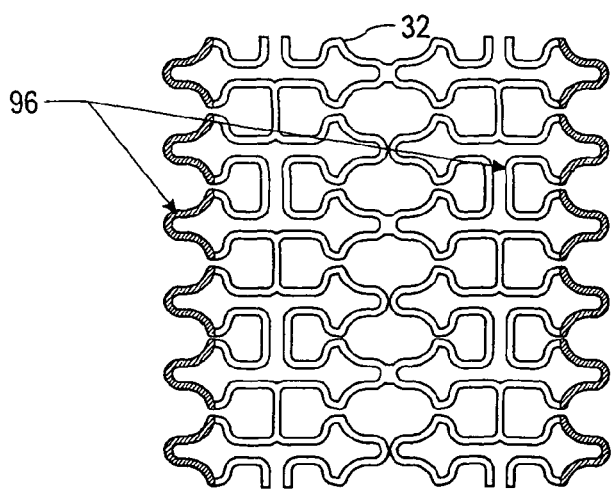

In order to confirm the positioning of the stent segments 32 on the expandable member 24, fluoroscopy is used to visualize the stent segments 32 relative to the markers 82 located on the inner shaft 27. In addition, by fluoroscopic visualization of the marker 56 located on the garage 55 at the distal end of the outer sheath 25, the user can see the extent of retraction of the sheath 25 relative to the expandable member 24 and view the location of the exposed stent segments 32 relative to the sheath 25. Visualization of the stent segments 32 is further enhanced with the use of radiopaque markers and/or materials in or on the stent segments themselves. Markers of radiopaque materials may be applied to the exterior of stent segments 32, e.g., by applying a metal such as gold, platinum, a radiopaque polymer, or other suitable coating or mark on all or a portion of the stent segments. Examples of such markers are illustrated in FIGS. 14A-B. In those Figures, radiopaque markers 95 are attached to a plurality of circular openings formed in the body of the stent segment 32. Six such markers are formed in a circumferentially aligned pattern in the FIG. 14A example, while three markers are formed in another circumferentially aligned pattern in the FIG. 14B example. The markers may be discs, buttons, or other members that are welded in place, or they may be provided as rivets or rivet-type members that are installed in a sized hole or eyelet. Alternatively, stent segments 32 may include a radiopaque cladding or coating or may be composed of radiopaque materials such as L-605 cobalt chromium (ASTM F90), other suitable alloys containing radiopaque elements, or multilayered materials having radiopaque layers. See, for example, FIGS. 15A-C, where three patterns of radiopaque coatings are illustrated. In FIG. 15A, a coating 96 of radiopaque material is provided in a broad circumferential center stripe on the stent segment 32. In FIGS. 15B and C, smaller circumferential stripes of radiopaque coatings 96 are formed on the proximal and distal ends of the stent segment 32, such as being formed only on the axial projection portions of the stent segment 32 (see FIG. 15C). In yet another alternative, stent segments 32 may have a geometry conducive to fluoroscopic visualization, such as having struts of greater thickness, sections of higher density, or overlapping struts.

Figure 15D:
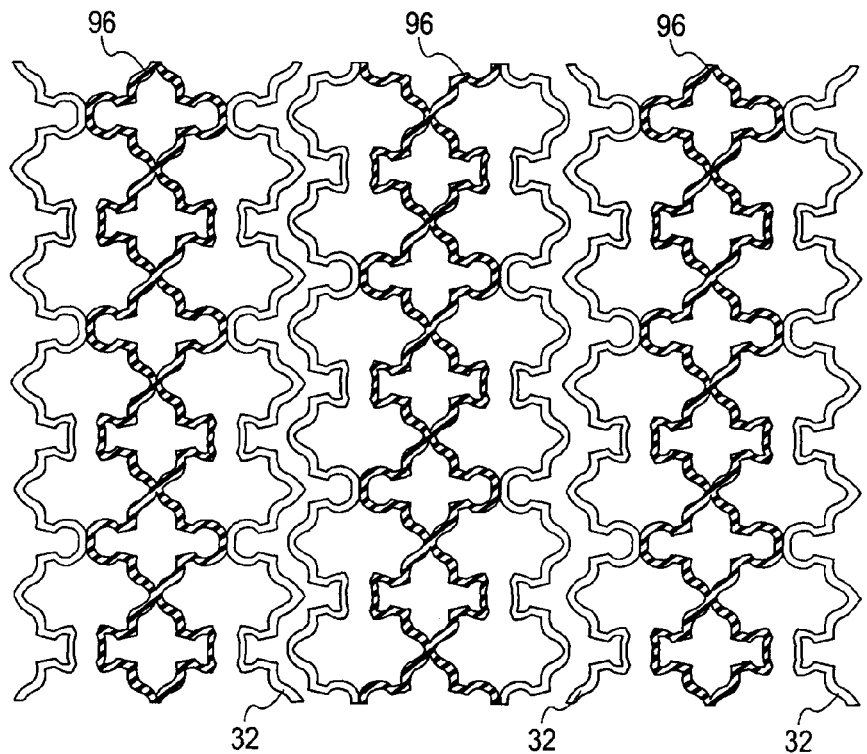
FIGS. 15D-E are side views of multiple stent segments in their expanded configurations having radiopaque marker coatings applied thereto.
Figure 15E:
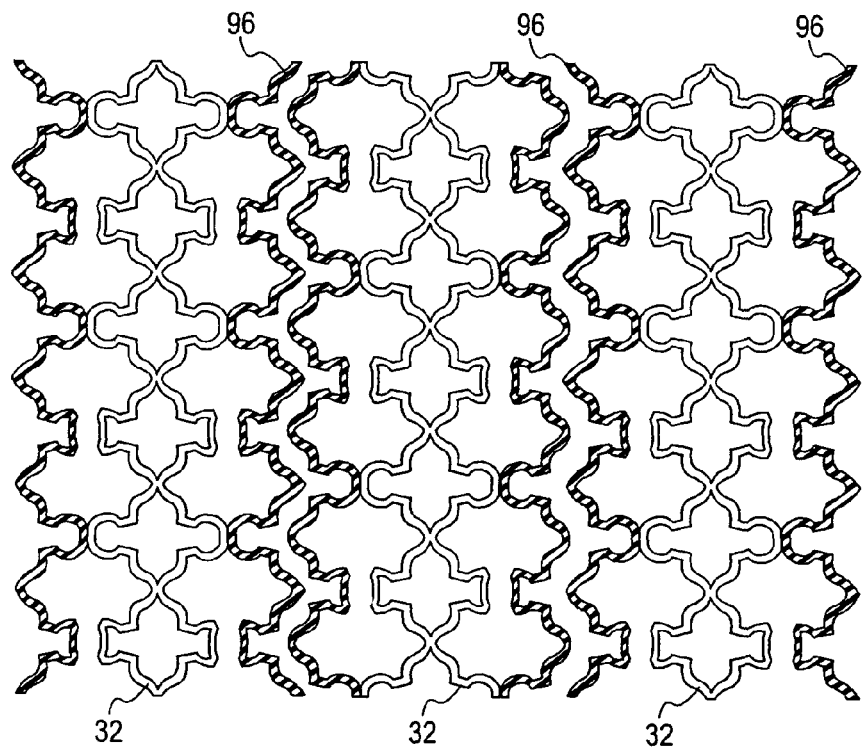

Preferably, the radiopaque markers are configured so as to provide an indication of the number, location, and/or relative spacing of each stent segment 32 when deployed end-to-end in a line in a vessel or other body lumen. This allows the operator to determine how many stent segments 32 have been deployed at a vascular site, and the spacing between adjacent stent segments 32. The radiopaque markers allow the operator to visualize with fluoroscopy the divisions between adjacent stent segments 32 by observing radiopaque markers on the ends and/or a middle portions of each stent segment 32. For example, in the embodiment of FIG. 15D, the operator may visualize a central stripe on each segment to allow an accounting of the number and location of deployed segments 32. In the embodiments of FIG. 15E, the operator may visualize two adjacent radiopaque stripes where two segment ends are disposed side-by-side. If the segments are close together, the operator sees a single wide stripe, while if the segments are separated by a gap, the operator may see two parallel stripes, thus providing an indication of the segment spacing as well as number.

Some of the possible materials that may be used in stent segments 32 include (by ASTM number):

F67-00 Unalloyed Titanium
F75-01 Cobalt-28 Chromium-6 Molybdenum Alloy
F90-01 Wrought Cobalt-20 Chromium-15 Tungsten-10 Nickel Alloy
F136-02a Wrought Titanium-6 Aluminum-4 Vanadium ELI Alloy
F138-00, F139-00 Wrought 18 Chromium-14 Nickel-2.5 Molybdenum Stainless Steel Bar or Sheet
F560-98 Unalloyed Tantalum
F562-02 Wrought 35 Cobalt-35 Nickel-20 Chromium-10 Molybdenum Alloy
F563-00 Wrought Cobalt-20 Nickel-20 Chromium 3.5 Molybdenum-3.5 Tungste-5 Iron Alloy
F688 Wrought Cobalt-35 Nickel-20 Chromium-10 Molybdenum Alloy
F745-00 18 Chromium-12.5 Nickel-2.5 Molybdenum Stainless Steel
F799-02 Cobalt-28 Chromium-6 Molybdenum Alloy
F961-96 Cobalt-35 Nickel-20 Chromium-10 Molybdenum Alloy
F1058-02 Wrought 40 Cobalt-20 Chromium-16 Iron-15 Nickel-7 Molybdenum Alloy
F1091-02 Wrought Cobalt-20 Chromium-15 Tungsten-10 Nickel Alloy
F1108 Titanium-6 Aluminum-4 Vanadium Alloy
F1295-01 Wrought Titanium-6 Aluminum-7 Niobium Alloy
F1314-01 Wrought Nitrogen-strengthened 22 Chromium-13 Nickel-5 Manganese-2.5 Molybdenum Stainless Steel Alloy
F1241-99 Unalloyed Titanium Wire
F1350-02 Wrought 18 Chromium-14 Nickel-2.5 Molybdenum Stainless Steel Wire
F1377-98a Cobalt-28 Chromium-6 Molybdenum Powder coating
F1472-02a Wrought Titanium-6 Aluminum-4 Vanadium Alloy
F1537-00 Wrought Cobalt-28 Chromium-6 Molybdenum Alloy
F1580-01 Titanium and Titanium-6 Aluminum-4 Vanadium Alloy Powder coating
F1586-02 Wrought Nitrogen Strengthened 21 Chromium-10 Nickel-3 Mnaganese-2.5 Molybdenum Stainless Steel Bar
F1713-96 Wrought Titanium-13 Niobium 13 Zirconium Alloy
F1813-01 Wrought Titanium-12 Molybdenum-6 Zirconium-2 Iron Alloy
F2063-00 Wrought Nickel-Titanium Shape Memory Alloys
F2066-01 Wrought Titanium-15 Molybdenum Alloy
F2146-01 Wrought Titanium-3 Aluminum-2.5 Vanadium Alloy Seamless Tubing
F2181-02a Wrought Stainless Steel Tubing.

Figure 5A:
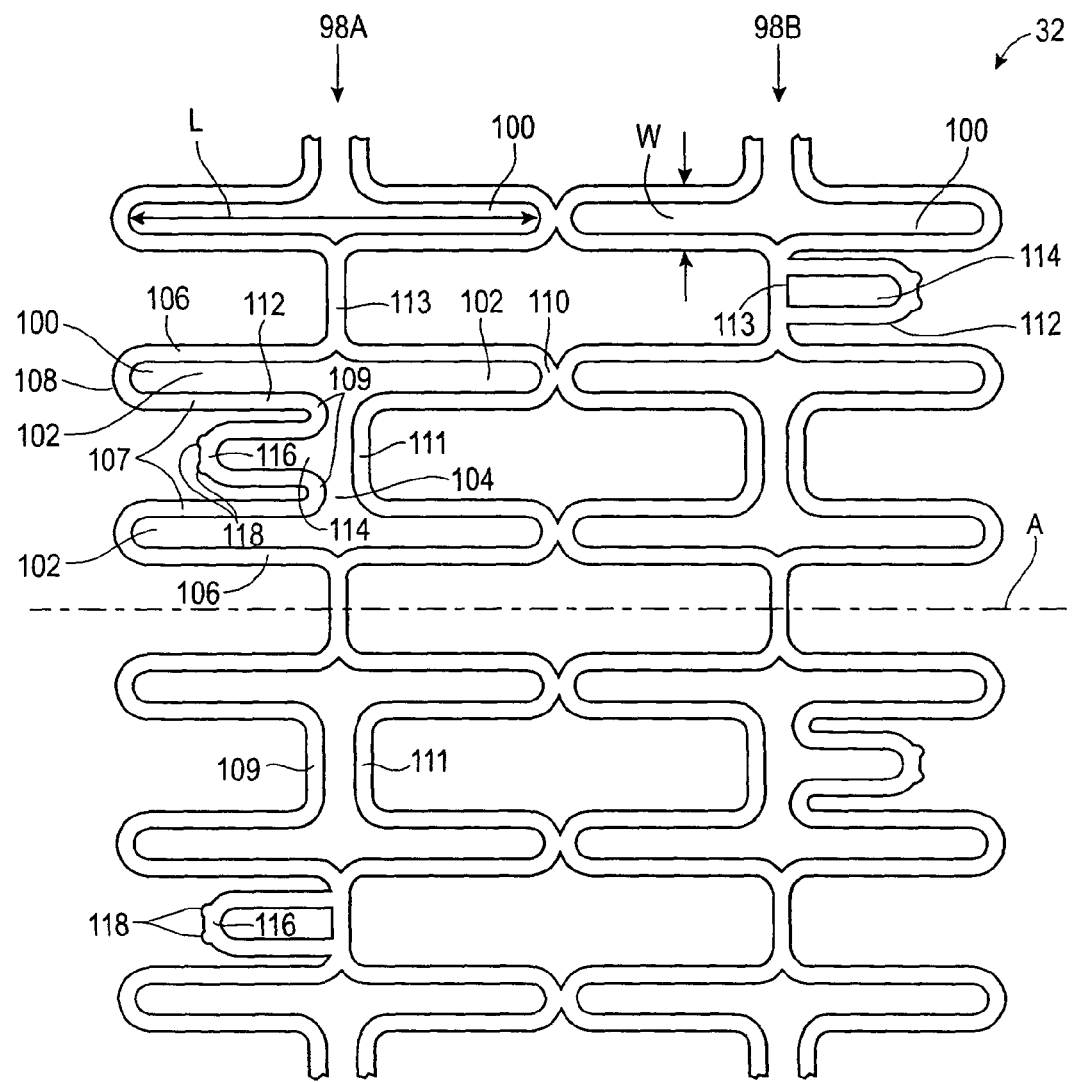
FIG. 5A is a side view of a first embodiment of a stent segment according to the invention in an unexpanded configuration.
Figure 5B:
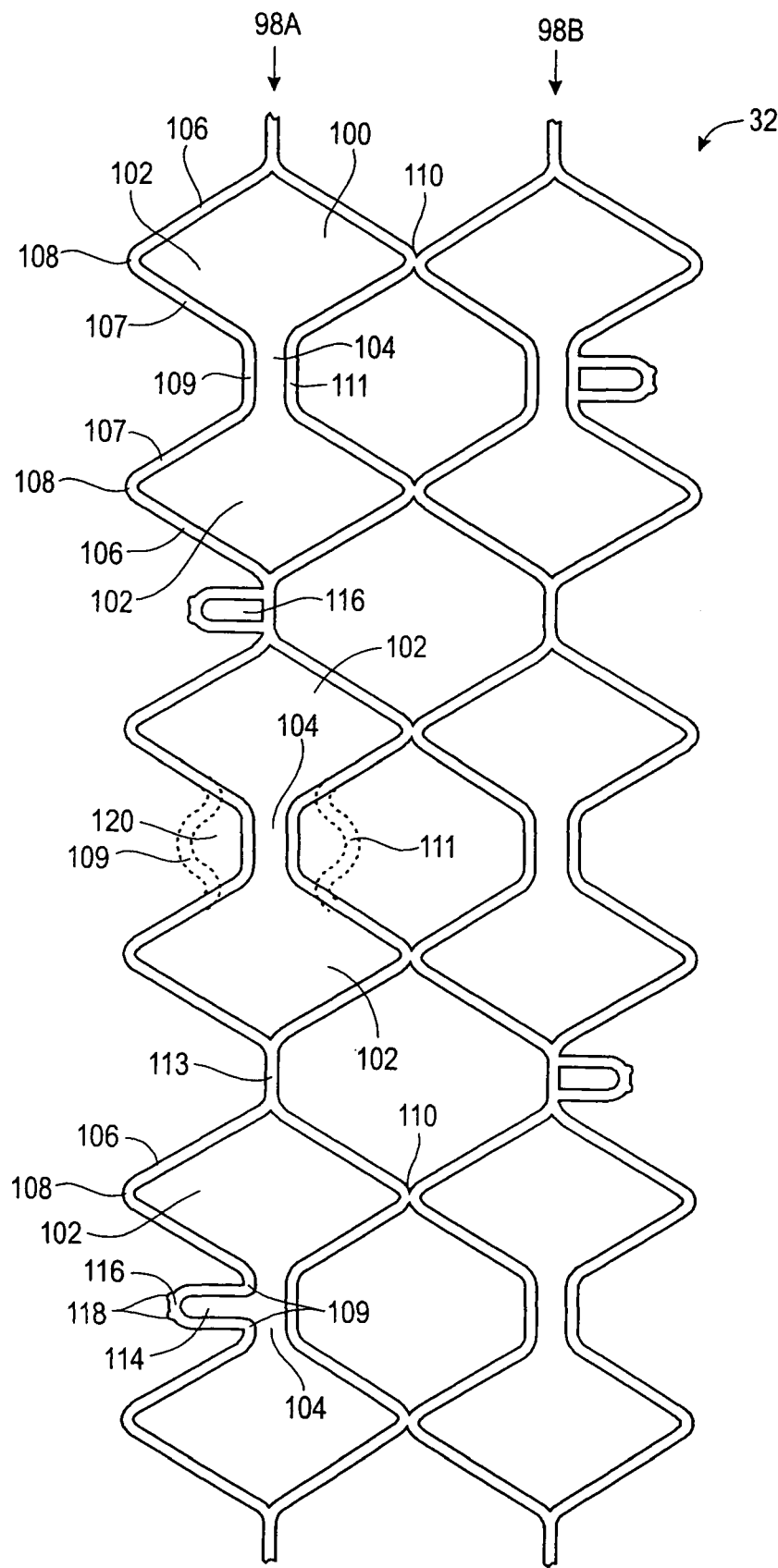
FIG. 5B is a side view of the stent segment of FIG. 5A in an expanded configuration.

FIGS. 5A-B illustrate a portion of a first embodiment of a stent segment 32. The Figures illustrate a portion of the stent segment 32 in a planar shape for clarity. The stent segment 32 includes two parallel rows 98A, 98B of I-shaped cells 100 formed into a cylindrical shape around an axial axis A. Each cell 100 includes upper and lower axial slots 102 and a connecting circumferential slot 104. The upper and lower slots 102 are bounded by upper axial struts 106, lower axial struts 107, curved outer ends 108 and curved inner ends 110. Each circumferential slot 104 is bounded by an outer circumferential strut 109 and an inner circumferential strut 111. Each I-shaped cell 100 is connected to the adjacent I-shaped cell 100 in the same row 98A or 98B by a circumferential connecting strut 113. All or a portion of cells 100 in row 98A merge or join with cells 100 in row 98B at the inner ends 110, which are integrally formed with the inner ends 110 of the adjacent cells 100.

In a preferred embodiment, a spacing member 112 extends outwardly in the axial direction from a selected number of outer circumferential struts 109 and/or connecting struts 113. Spacing member 112 preferably itself forms a subcell 114 in its interior, but alternatively may be solid without any cell or opening therein. For those spacing members 112 attached to outer circumferential struts 109, subcell 114 preferably communicates with I-shaped cell 100. Spacing members 112 are configured to engage the curved outer ends 108 of an adjacent stent segment 32 so as to maintain appropriate spacing between adjacent stent segments. In one embodiment, spacing members 112 have outer ends 116 with two spaced-apart protrusions 118 that provide a cradle-like structure to index and stabilize the curved outer end 108 of the adjacent stent segment. Preferably, spacing members 112 have an axial length of at least about 10%, more preferably at least about 25%, of the long dimension L of I-shaped cells 100, so that the I-shaped cells 100 of adjacent stent segments are spaced apart at least that distance. Because spacing members 112 experience little or no axial shortening during expansion of stent segments 32, this minimum spacing between stent segments is maintained both in the unexpanded and expanded configurations.

FIG. 5B shows stent segment 32 of FIG. 5A in an expanded configuration. It may be seen that cells 100 are expanded so that upper and lower slots 102 are diamond shaped with circumferential slots 104 remaining basically unchanged. This results in some axial shortening of the stent segment, thereby increasing the spacing between adjacent stent segments. The stent geometry is optimized by balancing the amount of axial shortening and associated inter-segment spacing, the desired degree of vessel wall coverage, the desired metal density, and other factors. Because the stent is comprised of multiple unconnected stent segments 32, any desired number from 2 up to 10 or more stent segments may be deployed simultaneously to treat lesions of any length. Further, because such segments are unconnected to each other, the deployed stent structure is highly flexible and capable of deployment in long lesions having curves and other complex shapes.

As an additional feature, circumferential slots 104 provide a pathway through which vessel side branches can be accessed for catheter interventions. Should stent segment 32 be deployed at a location in which it covers the ostium of a side branch to which access is desired, a balloon dilatation catheter may be positioned through circumferential slot 104 and expanded. This deforms circumferential struts 109, 111 axially outward, thereby expanding circumferential slot 104 and further expanding upper and lower slots 102, as shown in phantom in FIG. 5B. This provides a relatively large opening 120 through which a catheter may be inserted through stent segment 32 and into the side branch for placing stents, performing angioplasty, or carrying out other interventions.

Figure 6A:
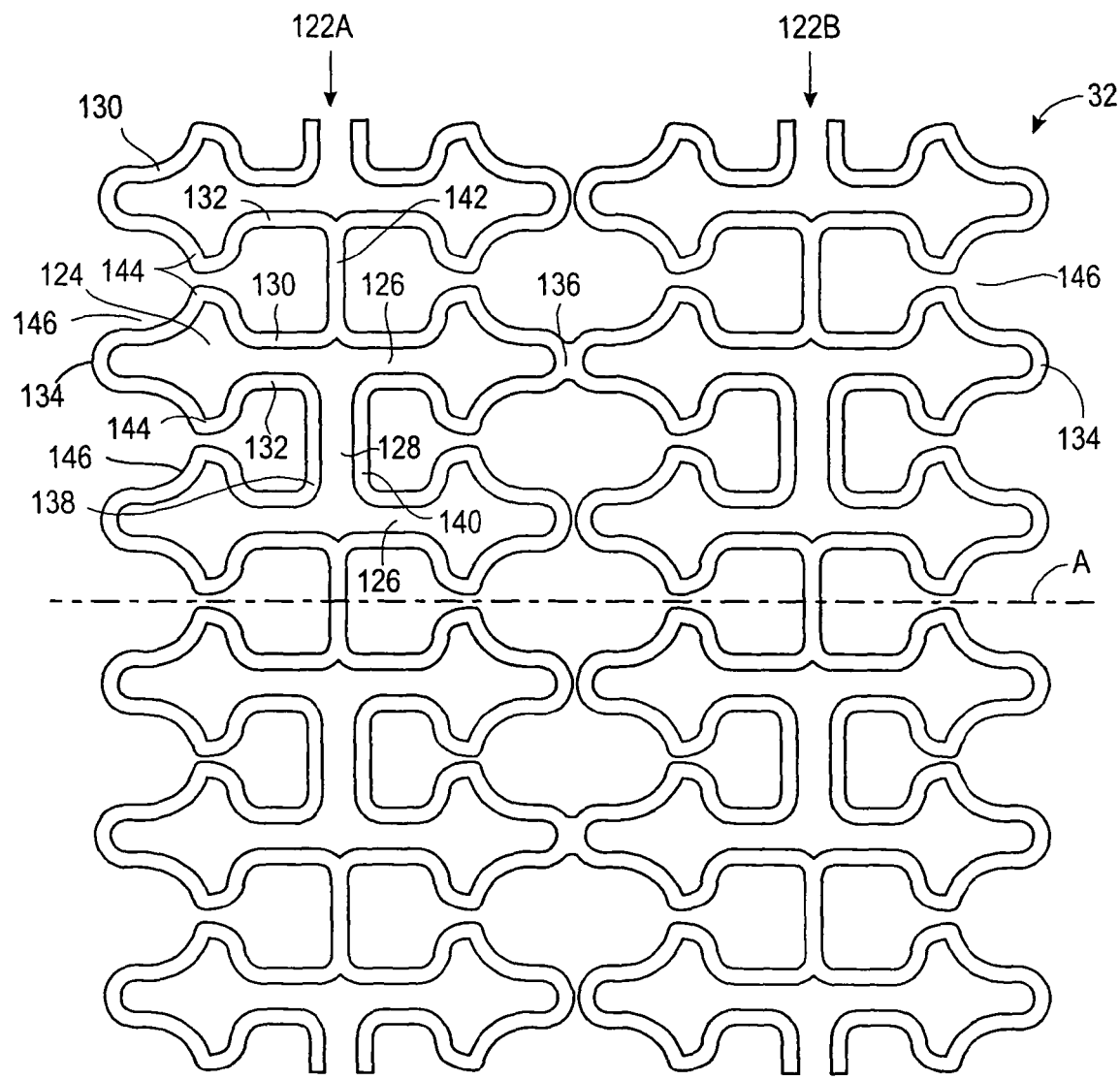
FIG. 6A is a side view of a second embodiment of a stent segment according to the invention in an unexpanded configuration.
Figure 6B:
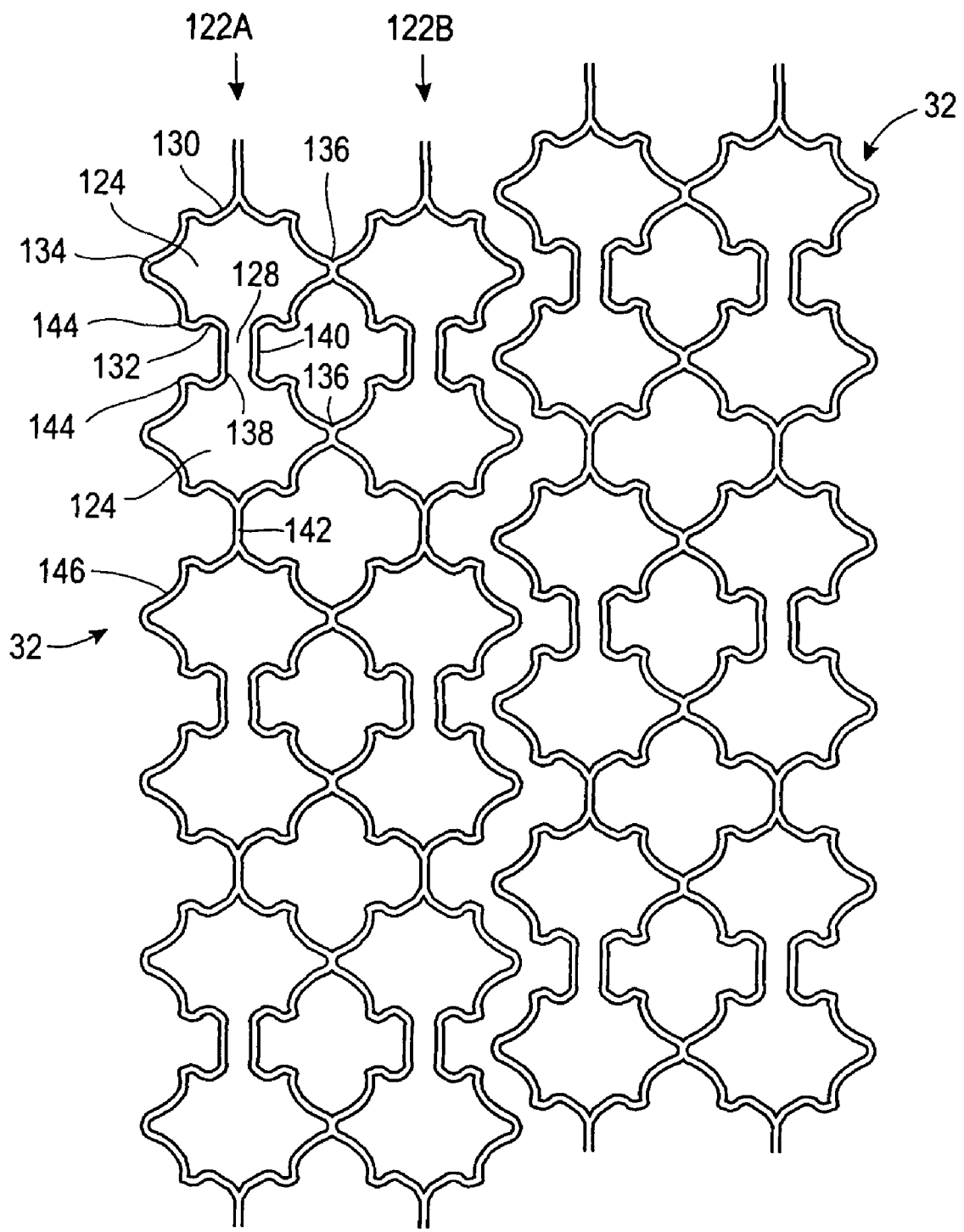
FIG. 6B is a side view of two of the stent segments of FIG. 6A in an expanded configuration.

FIGS. 6A-6B illustrate a second embodiment of a stent segment 32 according to the invention. In FIG. 6A, a portion of stent segment 32 is shown in a planar shape for clarity. Similar to the embodiment of FIG. 5A, stent segment 32 comprises two parallel rows 122A, 122B of I-shaped cells 124 formed into a cylindrical shape around axial axis A. Cells 124 have upper and lower axial slots 126 and a connecting circumferential slot 128. Upper and lower slots 126 are bounded by upper axial struts 130, lower axial struts 132, curved outer ends 134, and curved inner ends 136. Circumferential slots 128 are bounded by outer circumferential strut 138 and inner circumferential strut 140. Each I-shaped cell 124 is connected to the adjacent I-shaped cell 124 in the same row 122 by a circumferential connecting strut 142. Row 122A is connected to row 122B by the merger or joining of curved inner ends 136 of at least one (and preferably three) of upper and lower slots 126 in each cell 124.

One of the differences between the embodiment of FIGS. 6A-6B and that of FIGS. 5A-5B is the way in which spacing is maintained between adjacent stent segments. In place of the spacing members 112 of the earlier embodiment, the embodiment of FIG. 6A includes a bulge 144 in upper and lower axial struts 130, 132 extending circumferentially outwardly from axial slots 126. These give axial slots 126 an arrowhead or cross shape at their inner and outer ends. The bulge 144 in each upper axial strut 130 extends toward the bulge 144 in a lower axial strut 132 in the same cell 100 or in an adjacent cell 100, thus creating a concave abutment 146 in the space between each axial slot 126. Concave abutments 146 are configured to receive and engage curved outer ends 134 of cells 124 in the adjacent stent segment, thereby maintaining spacing between the stent segments. The axial location of bulges 144 along upper and lower axial struts 130, 132 may be selected to provide the desired degree of inter-segment spacing.

FIG. 6B shows two stent segments 32 of FIG. 6A in an expanded condition. It may be seen that axial slots 124 are deformed into a circumferentially widened modified diamond shape with bulges 144 on the now diagonal upper and lower axial struts 130, 132. Circumferential slots 128 are generally the same size and shape as in the unexpanded configuration. Bulges 144 have been pulled away from each other to some extent, but still provide a concave abutment 146 to maintain a minimum degree of spacing between adjacent stent segments. As in the earlier embodiment, some axial shortening of each segment occurs upon expansion and stent geometry can be optimized to provide the ideal intersegment spacing.

It should also be noted that the embodiment of FIGS. 6A-6B retains the feature described above with respect to FIGS. 5A-5B to enable access to vessel side branches blocked by stent segment 32. Should such side branch access be desired, a dilatation catheter may be inserted into circumferential slot 128 and expanded to provide an enlarged opening through which a side branch may be entered.

Referring now to FIGS. 7A-7E, the use of the stent delivery catheter of the invention will be described. While the invention will be described in the context of coronary artery treatment, it should be understood that the invention is useful in any of a variety of blood vessels and other body lumens in which stents are deployed, including the carotid, femoral, iliac and other arteries, as well as veins and other fluid-carrying vessels. A guiding catheter (not shown) is first inserted into a peripheral artery such as the femoral and advanced to the ostium of the target coronary artery. A guidewire GW is then inserted through the guiding catheter into the coronary artery A where lesion L is to be treated. The proximal end of guidewire GW is then inserted through nosecone 28 and guidewire tube 34 outside the patient's body and stent delivery catheter 20 is slidably advanced over guidewire GW and through the guiding catheter into the coronary artery A. Slider assembly 50 is positioned within the hemostasis valve at the proximal end of the guiding catheter, which is then tightened to provide a hemostatic seal with the exterior of the slider body 52. Stent delivery catheter 20 is positioned through a lesion L to be treated such that nosecone 28 is distal to lesion L. During this positioning, sheath 25 is positioned distally up to nosecone 28 so as to surround expandable member 24 and all of the stent segments 32 thereon.

Optionally, lesion L may be pre-dilated prior to stent deployment. Pre-dilation may be performed prior to introduction of stent delivery catheter 20 by inserting an angioplasty catheter over guidewire GW and dilating lesion L. Alternatively, stent delivery catheter 20 may be used for pre-dilation by retracting sheath 25 along with stent segments 32 to expose an extremity of expandable member 24 long enough to extend through the entire lesion. This may be done while delivery catheter 20 is positioned proximally of lesion L or with expandable member 24 extending through lesion L. Fluoroscopy enables the user to visualize the extent of sheath retraction relative to lesion L by observing the position of marker 56 on the garage 55 contained at the distal end of the sheath 25 relative to the markers 82 formed on the guidewire tube 34 beneath the expandable member 24. To allow stent segments 32 to move proximally relative to expandable member 24, force is released from pusher tube 86 and valve member 58 engages and draws the stent segments proximally with sheath 25. The pusher tube 86 is retracted along with the outer sheath 25 by use of an actuator provided on the handle 38. With the appropriate length of expandable member 24 exposed, expandable member 24 is positioned within lesion L and inflation fluid is introduced through inflation lumen 66 to inflate expandable member 24 distally of sheath 25 and thereby dilate lesion L. Expandable member 24 is then deflated and retracted within sheath 25 while maintaining force on pusher tube 86 so that stent segments 32 are positioned up to the distal end of expandable member 24, surrounded by sheath 25.

Following any predilatation, stent delivery catheter 20 is repositioned in artery A so that nosecone 28 is distal to lesion L as shown in FIG. 7A. Sheath 25 is then retracted as in FIG. 7B to expose the appropriate number of stent segments 32 to cover lesion L. Again, fluoroscopy can be used to visualize the position of sheath 25 by observing marker 56 thereon relative to marker 82 within expandable member 24. As sheath 25 is drawn proximally, force is maintained against pusher tube 86 so that stent segments 32 remain positioned up to the distal end of expandable member 24. It should also be noted that sheath 25 moves proximally relative to guidewire tube 34, which slides through guidewire tube exit port 35. Advantageously, regardless of the position of sheath 25, guidewire tube 34 provides a smooth and continuous passage for guidewire GW so that stent delivery catheter slides easily over guidewire GW.

With the desired number of stent segments 32 exposed distally of sheath 25, it is preferable to create some spacing between the stent segments to be deployed and those remaining enclosed within the sheath 25. This reduces the risk of dislodging or partially expanding the distal-most stent segment 32 within sheath 25 when expandable member 24 is inflated. Such spacing is created, as shown in FIG. 7C, by releasing force against pusher tube 86 and retracting both the pusher tube 86 and the sheath 25 a short distance simultaneously. The engagement of valve member 58 with stent segments 32 moves those stent segments 32 within sheath 25 away from those stent segments 32 distal to sheath 25. The length of this spacing is preferably equal to the length of about ½-1 stent segment, e.g., in one embodiment about 2-4 mm. By observing radiopaque marker 56 on sheath 25, the operator can adjust the spacing to be suitable in comparison to the length of marker 56, which preferably has a length equal to the desired spacing distance.

Expandable member 24 is then inflated by delivering inflation fluid through inflation lumen 66, as shown in FIG. 7D. The exposed distal portion of expandable member 24 expands so as to expand stent segments 32 thereon into engagement with lesion L. If predilatation was not performed, lesion L may be dilated during the deployment of stent segments 32 by appropriate expansion of expandable member 24. Sheath 25 constrains the expansion of the proximal portion of expandable member 24 and those stent segments 32 within sheath 25.

Figure 8:
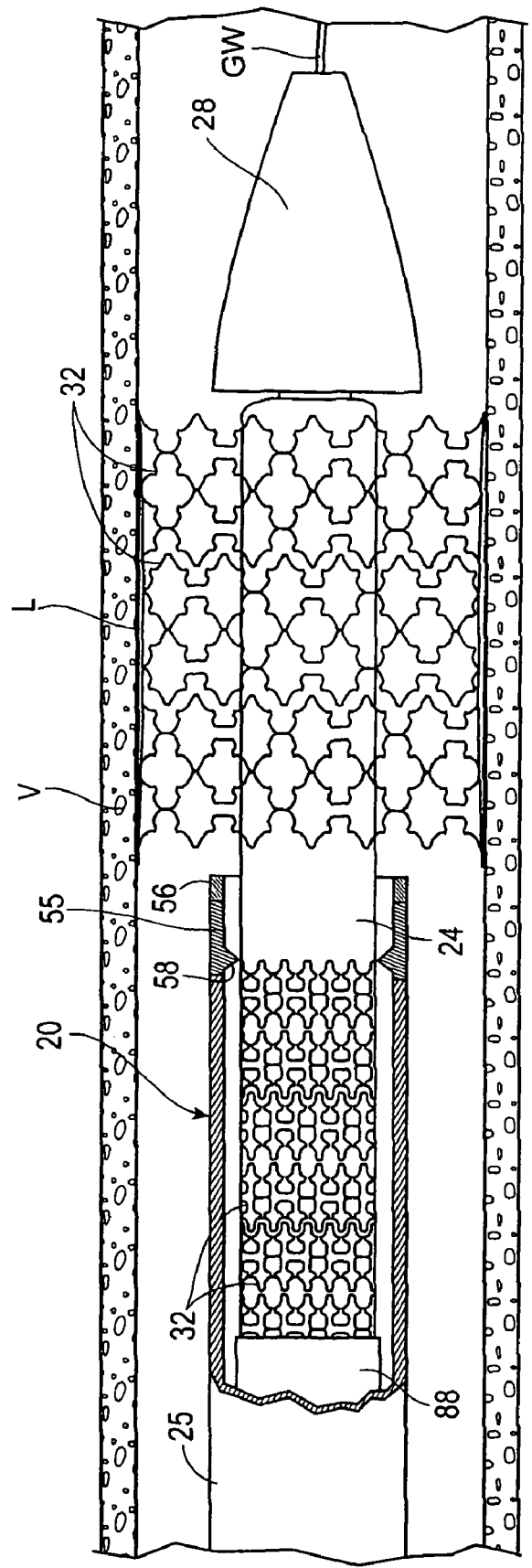
FIG. 8 is a side cut-away view of the stent delivery catheter of the invention positioned in a vessel with the stent segments of FIGS. 6A-6B in a deployed configuration.

Expandable member 24 is then deflated, leaving stent segments 32 in a plastically-deformed, expanded configuration within lesion L, as shown in FIG. 7E. The alternative embodiment of stent segment 32 illustrated in FIGS. 6A-6B is shown in a similarly expanded condition in FIG. 8. With stent segments 32 deployed, expandable member 24 may be retracted within sheath 25, again maintaining force against pusher tube 86 to slide stent segments 32 toward the distal end of expandable member 24. Expandable member 24 is moved proximally relative to stent segments 32 until the distal-most stent segment engages stop 78 (FIGS. 2A-2B), thereby placing stent segments 32 in position for deployment. Stent delivery catheter 20 is then ready to be repositioned at a different lesion in the same or different artery, and additional stent segments may be deployed. During such repositioning, guidewire tube 34 facilitates smooth tracking over guidewire GW. Advantageously, multiple lesions of various lengths may be treated in this way without removing stent delivery catheter 20 from the patient's body. Should there be a need to exchange stent delivery catheter 20 with other catheters to be introduced over guidewire GW, guidewire tube 34 facilitates quick and easy exchanges.

It should be understood that when the movement of the pusher tube, sheath, or stent segments is described in relation to other components of the delivery catheter of the invention, such movement is relative and will encompass both moving the sheath, pusher tube, or stent segments while keeping the other component(s) stationary, keeping the sheath, pusher tube or stent segments stationary while moving the other component(s), or moving multiple components simultaneously relative to each other.

While the foregoing description of the invention is directed to a stent delivery catheter for deploying stents into vascular lumens to maintain patency, it should be understood that various other types of wire-guided catheters also may embody the principles of the invention. For example, balloon catheters for angioplasty and other purposes, particularly those having a slidable external sheath surrounding the balloon, may be constructed in accordance with the invention. Other types of catheters for deployment of prosthetic devices such as embolic coils, stent grafts, aneurism repair devices, annuloplasty rings, heart valves, anastomosis devices, staples or clips, as well as ultrasound and angiography catheters, electrophysiological mapping and ablation catheters, and other devices may also utilize the principles of the invention.

Although the above is complete description of the preferred embodiments of the invention, various alternatives, additions, modifications and improvements may be made without departing from the scope thereof, which is defined by the claims.

What is claimed is:

1. Apparatus for performing an interventional procedure, comprising:
    a flexible catheter shaft having proximal and distal ends;
    a guidewire extending through a lumen in the distal end of said catheter shaft; and
    a sealing member having a first passage adapted to slidably receive the catheter shaft entirely through the sealing member in a fluid-tight sealed manner, and a second passage adapted to slidably receive the guidewire entirely through the sealing member in a fluid-tight sealed manner, the first and second passages being separate and spaced apart entirely through the sealing member, the sealing member being non-separable and comprised at least in part of a compliant elastomeric material forming the first and second passages which each maintain through-hole openings sized to receive the respective catheter shaft and guidewire,
    wherein the sealing member is adapted to be retained temporarily in a stationary position while the catheter shaft and guidewire remain freely slidable relative to the sealing member through each respective passage while remaining in sealing engagement therewith.

2. The apparatus of claim 1, further comprising a hemostatic valve adapted to receive and seal the sealing member.

3. The apparatus of claim 1, wherein said sealing member further comprises:
    an elongated slider tube;
    a slider body having a first recess at a first end and a second recess at a second end, said first recess adapted to fixedly engage an end portion of the slider tube;
    a slider seal adapted to be received and retained within the second recess of said slider body, said slider seal having a first through-hole adapted to slidably receive the catheter shaft in a substantially fluidly sealed manner, and a second through-hole adapted to slidably receive the guidewire in a substantially fluidly sealed manner; and a slider cap adapted to fixedly engage the second recess of the slider body such that said slider seal is retained within said second recess.

4. The apparatus of claim 3, wherein said slider tube includes a first through-hole adapted to slidably receive the catheter shaft and a second through-hole adapted to slidably receive the guidewire.

5. The apparatus of claim 3, wherein said slider body includes a first through-hole adapted to slidably receive the catheter shaft and a second through-hole adapted to slidably receive the guidewire.

6. The apparatus of claim 3, wherein said slider seal comprises a silicone compound.

7. The apparatus of claim 1, wherein at least a portion of the sealing member comprises a substantially incompressible material.

8. The apparatus of claim 2, wherein the hemostatic valve is sealed against an external surface of the sealing member.

9. The apparatus of claim 1, further comprising:
a tubular prosthesis releasably carried near the distal end of the catheter shaft, the tubular prosthesis being expandable to a shape suitable for engaging a target vessel;
a sheath disposed over the catheter shaft and the tubular prosthesis and being axially movable relative thereto, the sheath having proximal and distal ends and an exit port between the proximal and distal ends; and
a guidewire tube extending through the exit port and having a distal extremity disposed within the sheath and a proximal extremity disposed outside of the sheath, the guidewire tube being adapted for slidably receiving the guidewire therethrough.

* * * * *